(12) United States Patent
Blair et al.

(10) Patent No.: US 11,638,919 B2
(45) Date of Patent: May 2, 2023

(54) SAMPLE COLLECTION KIT INCLUDING CAP HAVING SELECTIVELY MOVABLE SLEEVE

(71) Applicant: Ancestry.com DNA, LLC, Lehi, UT (US)

(72) Inventors: Thomas E. Blair, Lehi, UT (US); Tyler Fredric Allan, Highland, UT (US); Bryce Twede, Provo, UT (US); Jeremy Johnson, Riverton, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 17/868,777

(22) Filed: Jul. 20, 2022

(65) Prior Publication Data

US 2022/0355300 A1   Nov. 10, 2022

Related U.S. Application Data

(63) Continuation of application No. 16/824,536, filed on Mar. 19, 2020, now Pat. No. 11,426,734, which is a
(Continued)

(51) Int. Cl.
*B01L 3/00* (2006.01)

(52) U.S. Cl.
CPC .......... *B01L 3/523* (2013.01); *B01L 3/50825* (2013.01); *B01L 2200/0689* (2013.01);
(Continued)

(58) Field of Classification Search
CPC ................. B01L 3/523; B01L 3/50825; B01L 2200/0689; B01L 2200/087;
(Continued)

(56) References Cited

U.S. PATENT DOCUMENTS

| 718,127 A | 1/1903 | Holmgren |
| D169,994 S | 7/1953 | Soffer et al. |

(Continued)

FOREIGN PATENT DOCUMENTS

| EP | 3235441 A1 | 10/2017 |
| JP | 2008-518858 A | 6/2008 |

(Continued)

OTHER PUBLICATIONS

European Patent Office, Extended European Search Report and Opinion, EP Patent Application No. 18881701.9, dated Jul. 1, 2021, eight pages.
(Continued)

*Primary Examiner* — Jennifer Wecker
*Assistant Examiner* — Oyeleye Alexander Alabi
(74) *Attorney, Agent, or Firm* — Fenwick & West LLP

(57) ABSTRACT

A sample collection system can include a sample collection vessel having a sample collection chamber with an opening configured to receive a sample into the sample collection chamber. The sample collection system can additionally include a selectively movable sleeve valve configured to associate with the opening of the sample collection chamber. The sample collection system can include a sealing cap that is configured to associate with the selectively movable sleeve valve and with the sample collection vessel. The sealing cap can include a reagent chamber having reagent(s) stored therein, and when the sealing cap is associated with the sample collection vessel, the selectively movable sleeve valve opens, dispensing the reagent(s) into the sample collection chamber. When the selectively moveable sleeve associates with the sample collection chamber, an outer sleeve slides relative to an inner vessel, opening the sleeve and dispensing reagent into the sample collection chamber.

20 Claims, 14 Drawing Sheets

Related U.S. Application Data continuation-in-part of application No. 16/198,480, filed on Nov. 21, 2018, now Pat. No. 11,311,884.

(60) Provisional application No. 62/820,618, filed on Mar. 19, 2019, provisional application No. 62/625,187, filed on Feb. 1, 2018, provisional application No. 62/590,165, filed on Nov. 22, 2017.

(52) U.S. Cl.
CPC ..... *B01L 2200/087* (2013.01); *B01L 2200/16* (2013.01); *B01L 2300/042* (2013.01); *B01L 2300/047* (2013.01); *B01L 2300/049* (2013.01); *B01L 2300/0832* (2013.01)

(58) Field of Classification Search
CPC ........... B01L 2200/16; B01L 2300/042; B01L 2300/047; B01L 2300/049; B01L 2300/0832; B01L 2200/025; B01L 2200/0684; B01L 2200/141; B01L 2200/18; B01L 2300/123; A61B 10/0096
See application file for complete search history.

(56) References Cited

U.S. PATENT DOCUMENTS

| | | |
|---|---|---|
| D175,257 S | 8/1955 | Hopkins |
| 2,793,776 A | 5/1957 | Ipari |
| D196,112 S | 8/1963 | Esser |
| 3,831,742 A | 8/1974 | Gardella et al. |
| 4,131,016 A | 12/1978 | Layton |
| 4,184,483 A | 1/1980 | Greenspan |
| 4,217,798 A | 8/1980 | McCarthy et al. |
| 4,301,812 A | 11/1981 | Layton et al. |
| 4,312,950 A | 1/1982 | Snyder et al. |
| D277,736 S | 2/1985 | Long |
| D286,546 S | 11/1986 | Funahashi |
| 4,935,342 A | 6/1990 | Seligson et al. |
| 4,982,553 A | 1/1991 | Itoh |
| D330,011 S | 10/1992 | Miller |
| 5,283,038 A | 2/1994 | Seymour |
| 5,393,496 A | 2/1995 | Seymour |
| 5,396,986 A | 3/1995 | Fountain et al. |
| D362,623 S | 9/1995 | Ma |
| 5,714,341 A | 2/1998 | Thieme et al. |
| D392,187 S | 3/1998 | King |
| 5,736,322 A | 4/1998 | Goldstein |
| 5,736,355 A | 4/1998 | Dyke et al. |
| 5,830,154 A | 11/1998 | Goldstein et al. |
| 5,830,410 A | 11/1998 | Thieme et al. |
| D412,107 S | 7/1999 | Bosshardt |
| 5,927,549 A | 7/1999 | Wood |
| 5,933,498 A | 8/1999 | Schneck et al. |
| 6,003,728 A | 12/1999 | Elliott |
| 6,048,091 A | 4/2000 | McIntyre et al. |
| 6,152,296 A | 11/2000 | Shih |
| D437,786 S | 2/2001 | van Swieten et al. |
| 6,228,323 B1 | 5/2001 | Asgharian et al. |
| 6,428,962 B1 | 8/2002 | Naegele |
| 6,458,546 B1 | 10/2002 | Baker |
| D470,240 S | 2/2003 | Niedbala et al. |
| D471,234 S | 3/2003 | Okutani |
| 6,543,612 B2 | 4/2003 | Lee et al. |
| 6,548,256 B2 | 4/2003 | Lienau et al. |
| D474,280 S | 5/2003 | Niedbala et al. |
| 6,627,152 B1 | 9/2003 | Wong |
| 6,786,330 B2 | 9/2004 | Mollstam et al. |
| D507,351 S | 7/2005 | Birnboim |
| 6,939,672 B2 | 9/2005 | Lentrichia et al. |
| 6,992,182 B1 | 1/2006 | Muller et al. |
| D515,435 S | 2/2006 | Muehlhausen |
| 7,055,685 B1 | 6/2006 | Patterson et al. |
| D537,416 S | 2/2007 | Fortin et al. |
| 7,178,683 B2 | 2/2007 | Birkmayer et al. |
| 7,214,484 B2 | 5/2007 | Weber et al. |
| 7,297,485 B2 | 11/2007 | Bomar et al. |
| 7,303,876 B2 | 12/2007 | Greenfield et al. |
| D573,465 S | 7/2008 | Kogure et al. |
| D574,507 S | 8/2008 | Muir et al. |
| D584,357 S | 1/2009 | Oka |
| 7,482,116 B2 | 1/2009 | Birnboim |
| D586,856 S | 2/2009 | Yagyu |
| 7,537,132 B2 | 5/2009 | Marple et al. |
| 7,544,468 B2 | 6/2009 | Goldstein et al. |
| 7,589,184 B2 | 9/2009 | Hogan et al. |
| 7,645,424 B2 | 1/2010 | O'Donovan |
| D612,730 S | 3/2010 | Rushe |
| 7,748,550 B2 | 7/2010 | Cho |
| 7,854,104 B2 | 12/2010 | Cronin |
| 7,858,396 B2 | 12/2010 | Corstjens et al. |
| D631,350 S | 1/2011 | Beach et al. |
| D631,553 S | 1/2011 | Niedbala et al. |
| D640,794 S | 6/2011 | Sunstrum et al. |
| D640,795 S | 6/2011 | Jackson et al. |
| 7,998,757 B2 | 8/2011 | Darrigrand et al. |
| 8,038,668 B2 | 10/2011 | Scott et al. |
| 8,062,908 B2 | 11/2011 | Mink et al. |
| 8,158,357 B2 | 4/2012 | Birnboim et al. |
| 8,221,381 B2 | 7/2012 | Muir et al. |
| D673,265 S | 12/2012 | Nonnemacher et al. |
| 8,425,864 B2 | 4/2013 | Haywood et al. |
| 8,431,384 B2 | 4/2013 | Hogan et al. |
| 8,470,536 B2 | 6/2013 | Birnboim et al. |
| D693,682 S | 11/2013 | Bahri et al. |
| 8,673,239 B2 | 3/2014 | Niedbala et al. |
| 8,728,414 B2 | 5/2014 | Beach et al. |
| D718,127 S | 11/2014 | Moriyama |
| 9,040,675 B2 | 5/2015 | Bales et al. |
| 9,072,499 B2 | 7/2015 | Birnboim et al. |
| 9,079,181 B2 | 7/2015 | Curry et al. |
| D743,044 S | 11/2015 | Jackson et al. |
| D743,571 S | 11/2015 | Jackson et al. |
| 9,207,164 B2 | 12/2015 | Muir et al. |
| D757,546 S | 5/2016 | Seifer |
| 9,410,147 B2 | 8/2016 | Gundling |
| 9,416,356 B2 | 8/2016 | Gundling |
| 9,523,115 B2 | 12/2016 | Birnboim |
| D775,953 S | 1/2017 | Ruthe-Steinsiek |
| D777,111 S | 1/2017 | Zantout et al. |
| 9,732,376 B2 | 8/2017 | Oyler et al. |
| 9,757,179 B2 | 9/2017 | Formica |
| D811,882 S | 3/2018 | Gundersen |
| 10,000,795 B2 | 6/2018 | Birnboim et al. |
| D843,834 S | 3/2019 | Gundersen |
| D850,647 S | 6/2019 | Jackson et al. |
| 10,435,735 B2 | 10/2019 | Birnboim et al. |
| 2003/0089627 A1 | 5/2003 | Chelles et al. |
| 2004/0132091 A1 | 7/2004 | Ramsey et al. |
| 2006/0201948 A1 | 9/2006 | Ellson et al. |
| 2007/0170142 A1 | 7/2007 | Cho |
| 2009/0024060 A1 | 1/2009 | Darrigrand et al. |
| 2009/0133366 A1 | 5/2009 | Cronin et al. |
| 2009/0216213 A1 | 8/2009 | Muir et al. |
| 2010/0099149 A1 | 4/2010 | Birnboim et al. |
| 2010/0258457 A1 | 10/2010 | Seelhofer |
| 2011/0020195 A1 | 1/2011 | Luotola |
| 2011/0207621 A1 | 8/2011 | Montagu et al. |
| 2011/0212002 A1 | 9/2011 | Curry et al. |
| 2012/0024861 A1 | 2/2012 | Otsuka et al. |
| 2012/0024862 A1 | 2/2012 | Otsuka et al. |
| 2012/0046574 A1 | 2/2012 | Skakoon |
| 2012/0061392 A1 | 3/2012 | Beach et al. |
| 2013/0092690 A1 | 4/2013 | Skakoon |
| 2013/0164738 A1 | 6/2013 | Becker |
| 2014/0120531 A1* | 5/2014 | Biadillah ............ A61B 10/007 435/7.1 |
| 2014/0316302 A1 | 10/2014 | Nonnemacher et al. |
| 2015/0056716 A1 | 2/2015 | Oyler et al. |
| 2016/0262679 A1 | 9/2016 | Ivosevic et al. |
| 2017/0001191 A1 | 1/2017 | Biadillah et al. |
| 2017/0072393 A1 | 3/2017 | Jackson et al. |
| 2017/0130219 A1 | 5/2017 | Birnboim et al. |
| 2017/0166955 A1 | 6/2017 | Birnboim et al. |

(56) References Cited

U.S. PATENT DOCUMENTS

| | | | |
|---|---|---|---|
| 2017/0226469 | A1 | 8/2017 | Birnboim et al. |
| 2019/0151842 | A1 | 5/2019 | Williams et al. |
| 2019/0210778 | A1 | 7/2019 | Muir et al. |
| 2019/0358628 | A1 | 11/2019 | Curry et al. |

FOREIGN PATENT DOCUMENTS

| | | |
|---|---|---|
| JP | 2010/213660 A | 9/2010 |
| JP | 2014-527615 A | 10/2014 |
| JP | 2017-194324 A | 10/2017 |
| WO | WO-98/03265 | 1/1998 |
| WO | WO 2012/177656 A2 | 12/2012 |
| WO | WO 2015/017701 A1 | 2/2015 |
| WO | WO 2015/112496 A2 | 7/2015 |
| WO | WO 2016/178132 A1 | 11/2016 |

OTHER PUBLICATIONS

Meulenbel T, I. et al. "High-Yield Noninvasive Human Genomic DNA Isolation Method for Genetic Studies in Geographically Dispersed Families and Populations," American Journal of Human Genetics, 1995, vol. 57, No. 1252-1254, 3 pages.

PCT International Search Report and Written Opinion, PCT Application No. PCT/US2020/023711, dated Jul. 16, 2020, 12 pages.

PCT International Search Report and Written Opinion, PCT Application No. PCT/US2018/062312, dated Mar. 19, 2019, fifteen pages.

\* cited by examiner

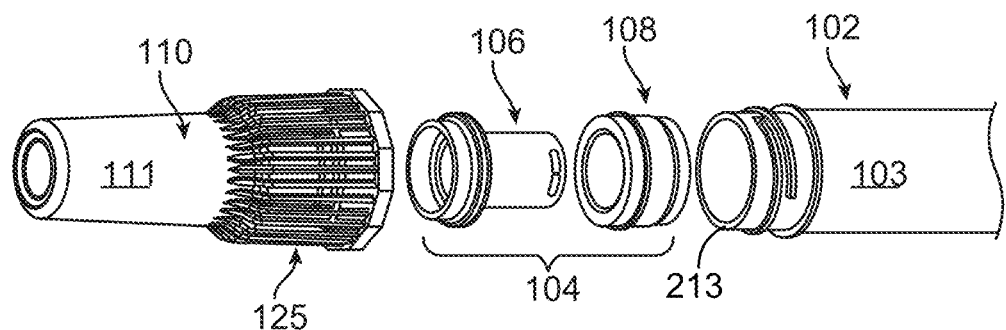
FIG. 1
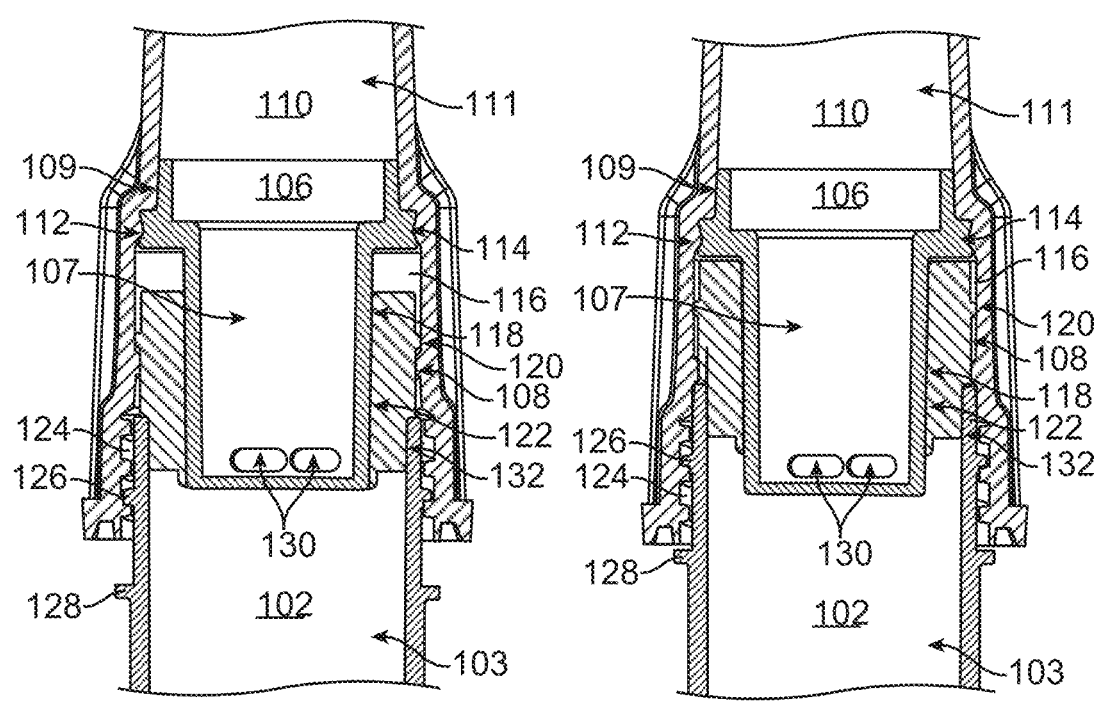
FIG. 2
FIG. 3

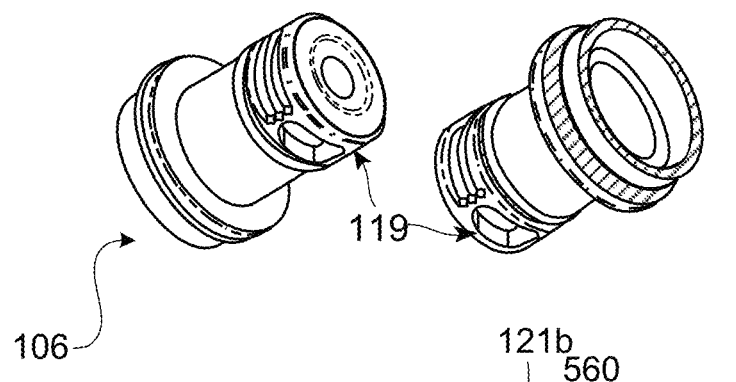
FIG. 5D
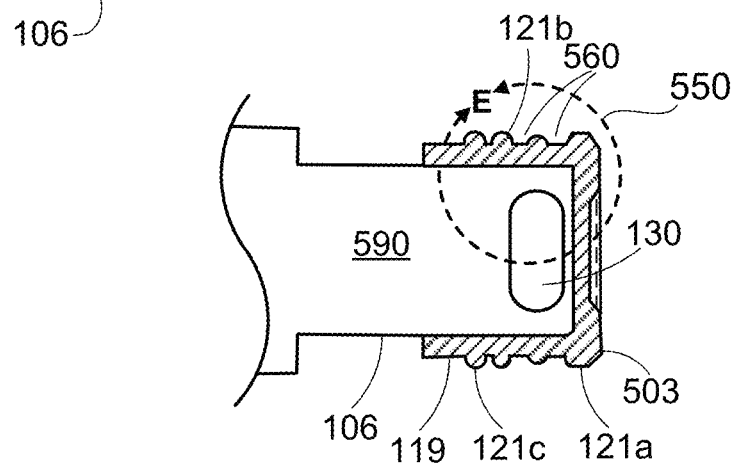
FIG. 5E
FIG. 5F
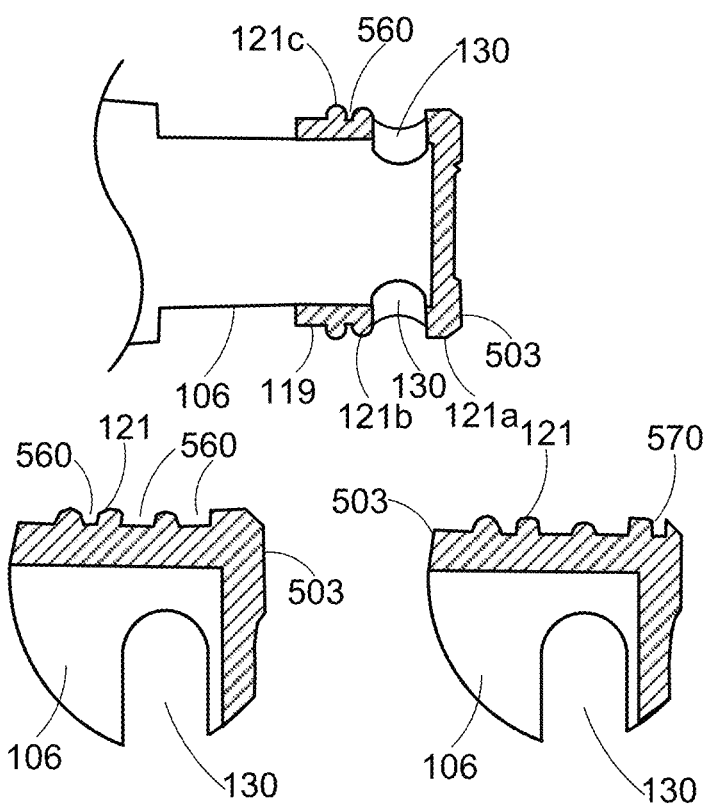
FIG. 5G

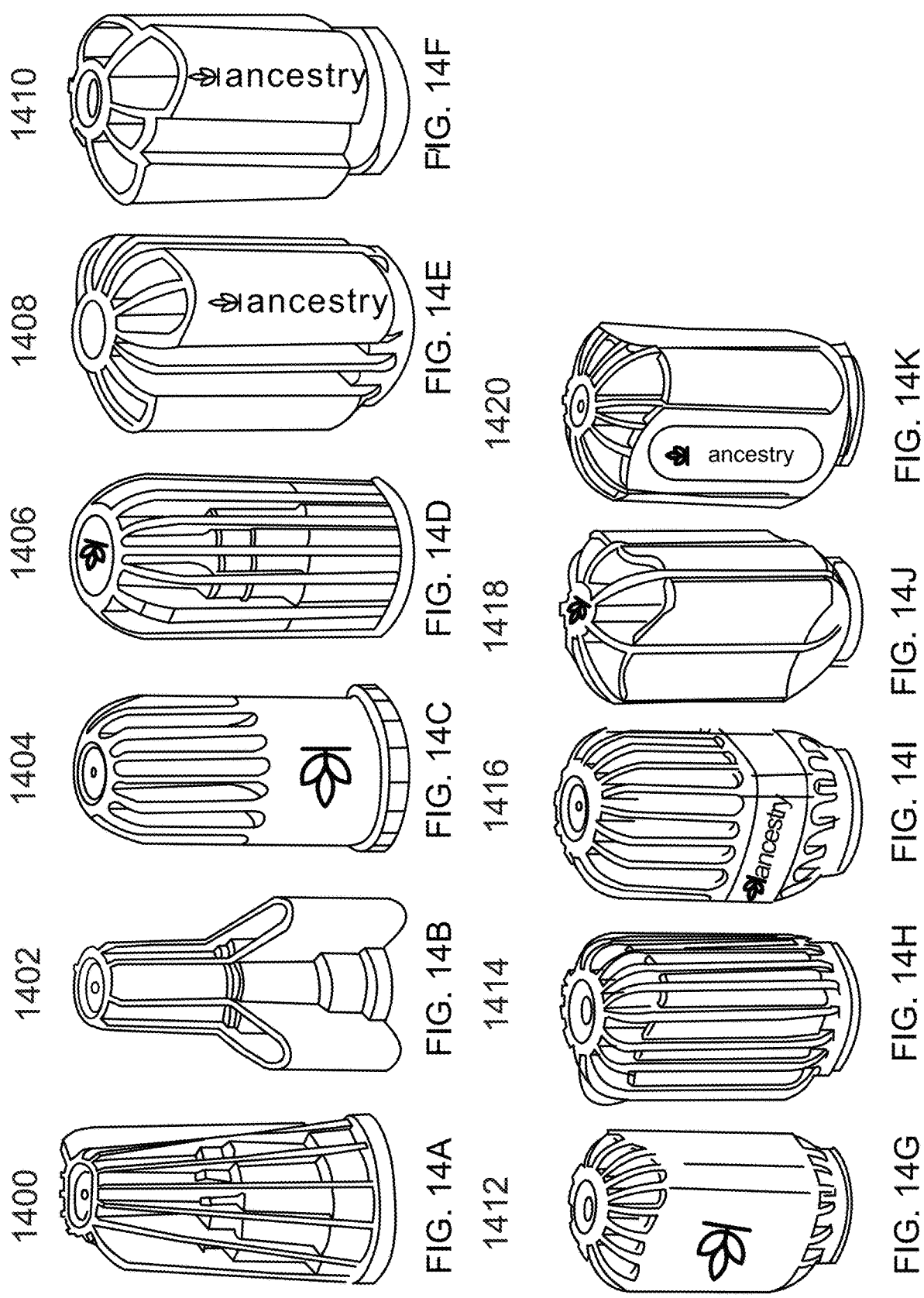

SAMPLE COLLECTION KIT INCLUDING CAP HAVING SELECTIVELY MOVABLE SLEEVE

CROSS-REFERENCE TO RELATED APPLICATIONS

The present application is a continuation of U.S. patent application Ser. No. 16/824,536, Filed Mar. 19, 2020, which claims the benefit of U.S. Provisional Patent Application No. 62/820,618 filed on Mar. 19, 2019. U.S. patent application Ser. No. 16/824,536 is also a continuation-in-part of U.S. patent application Ser. No. 16/198,480, (now U.S. Pat. No. 11,311,884), filed on Nov. 21, 2018, which claims the benefit of U.S. Provisional Patent Application 62/625,187, filed on Feb. 1, 2018, and the benefit of U.S. Provisional Patent Application 62/590,165, filed on Nov. 22, 2017. All of the foregoing are hereby incorporated by reference in their entirety.

BACKGROUND

This disclosure generally relates to vials and vessels for collecting and storing biological samples. More specifically, the present disclosure relates to systems and kits for the collection and preservation of biological samples for future testing in a laboratory or other biological sample analysis facility.

Field collection of biological samples can provide scientists, physicians, geneticists, epidemiologists, or similar personnel with invaluable information. For example, access to a fresh sample of a patient's blood, purulent discharge, or sputum can help a physician or epidemiologist to isolate or identify a causative agent of infection. Similarly, a saliva sample can permit a scientist or geneticist access to the requisite nucleic acid for genetic sequencing, phenotyping, or other genetic-based studies. In the foregoing examples, in addition to many other situations, it is desirable to work with a fresh biological sample to ensure procurement of accurate results. However, isolation of the probative composition (e.g., nucleic acid, proteins, chemicals, etc.) often requires the use of specialized equipment and often benefits from controlled laboratory conditions.

It can be inconvenient and sometimes improbable to require patients/individuals to travel to a biological sample collection center having the appropriate equipment and desirable controlled environment for sample preparation. Similarly, it may be difficult for personnel to directly access the patient/individual, particularly if the sample size is large and/or geographically diverse (e.g., as can be found in large genetic studies of thousands of individuals across an entire country, ethnic population, or geographic region). Further complicating this issue, it is often beneficial to immediately process any procured biological sample, and field personnel may be limited by lack of access to appropriate specialized equipment or a controlled environment for high-fidelity sample processing.

Some biological sample collection devices and kits have addressed some of the foregoing issues. For example, some commercial kits provide a user with a vial for receiving a biological sample and a preservation reagent that can be added to the collected biological sample, acting to preserve elements within the biological sample (to a certain extent and for a period of time). However, implementations of self-collection systems often rely on inexperienced or untrained individuals to deposit the biological sample into the receiving vessel. This presents a number of problems, including, for example, technical training and precise measurements often required to properly preserve the biological sample for later processing. In the absence of such, it is important to provide a biological sample collection system that can be easily implemented by a novice user and which can preserve the received biological sample for later processing.

Accordingly, there are a number of disadvantages with biological sample collection and preservations systems that can be addressed.

SUMMARY

Implementations of the present disclosure solve one or more of the foregoing or other problems in the art with kits, apparatus, and methods for collecting and preserving a sample, for example a biological sample. In particular, in one or more implementations the kit is a biological sample collection system for collecting and preserving a biological sample. The biological sample collection system can include a sample collection vessel for receiving a biological sample and a sealing cap configured to removably engage with the sample collection vessel. The biological sample collection system can also include an inner vessel securely engaged with the sealing cap and Figured to store a measure of reagent(s). The inner vessel may be further configured with a body and fluid vent located on the body. An outer sleeve frictionally engages with the inner vessel while sliding translationally relative to the inner vessel between a first position and a second position. In the first position, the outer sleeve covers the fluid vent and in the second position opens the fluid vent. When the sample collection vessel is fully engaged with the sealing cap, the sample collection vessel is configured to push the outer sleeve to the second position, thereby opening the fluid vent.

In another implementation, a sealing cap removably engages with a sample collection vessel to receive a biological sample. The sealing cap comprises an outer cap, an inner vessel for storing a measure of reagent(s), and an outer sleeve to frictionally engage with the inner vessel. The inner vessel further comprises a body and a fluid vent located on the body. The outer sleeve is configured to slide translationally relative to the inner vessel between a first position covering the fluid vent and a second position opening the fluid vent.

In another implementation, a biological sample collection system includes a sample collection vessel for receiving a biological sample, a sealing cap configured to removably engage with the sample collection vessel, an inner vessel securely engaged with the sealing cap to store a measure of reagent. The inner vessel is further comprised of a cylindrical body including a fluid vent and raised surface areas on the cylindrical body to surround the fluid vent. The biological sample collection system further includes an outer sleeve movably engaged with the inner vessel and in contact with the outer sleeve. The outer sleeve is configured to cover the fluid vent when the sealing cap is disengaged from the sample collection vessel and to be moved relative to the inner vessel to open the fluid vent when the sealing cap is engaged with the sample collection vessel. When moved to open the fluid vent, the reagent is dispensed into the sample collection chamber through the fluid vent.

Accordingly, systems, methods, and kits for collecting a biological sample are disclosed herein. This summary is provided to introduce a selection of concepts in a simplified form that is further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 1 illustrates an exploded perspective view of a three-dimensional model of a sample collection system that includes a cap configured to receive a selectively movable sleeve valve.

FIG. 2 illustrates a cross-sectional view of an assembled sample collection system with a selectively movable sleeve valve depicted in a closed position.

FIG. 3 illustrates a cross-sectional view of the assembled sample collection system of FIG. 2 with the selectively movable sleeve valve is depicted in an open position.

FIGS. 5B-5G illustrate various views of an inner vessel with raised surface areas.

DETAILED DESCRIPTION

Figure 4:
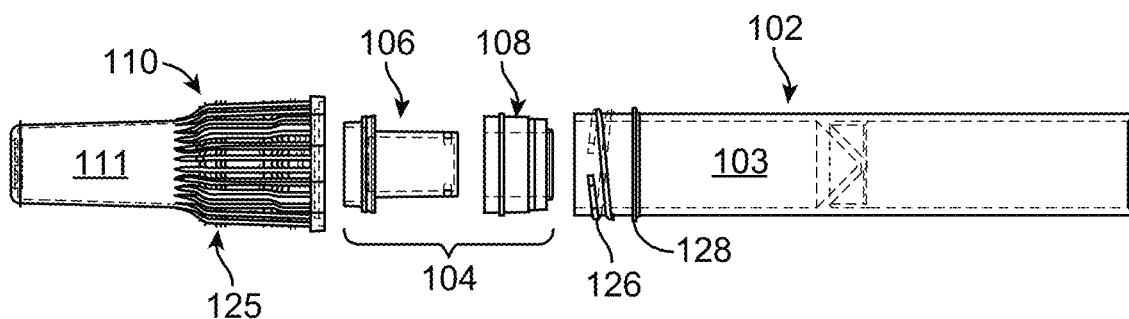
FIG. 4 illustrates an exploded elevation view of a sample collection system, similar to the three-dimensional model depicted in FIG. 1, that includes a cap configured to receive a selectively movable sleeve valve.

Embodiments of the present disclosure address one or more problems in the art of systems, kits, and/or methods for collecting and preserving a biological sample. A biological sample can be collected and its contents evaluated for various reasons, including, for example, identifying or characterizing a causative agent of disease (e.g., for treatment of the affected individual, for epidemiological reasons, etc.) or for genetic analysis of a subject's nucleic acid (e.g., genetic phenotyping, gene expression studies, genome sequencing, etc.). In most instances, including within the foregoing examples, it is desirous that the fidelity of the biological sample is maintained so that it retains its probative value. However, collecting and preparing biological samples for analysis has traditionally been an endeavor for the skilled technician or specialized professional. This is problematic for obvious reasons, including the time and cost associated with individually collecting and transporting biological samples, particularly when the subjects reside in disparate rural locations and require service from personnel with the proper skill set to properly collect and preserve the biological sample.

Embodiments of the present disclosure provide sample collection and preservation systems and kits, and methods for using the same, which address one or more of the foregoing problems. For example, utilizing systems, kits, and methods for collecting and preserving biological samples, as disclosed herein, remove the need for specialized personnel when collecting and initially preserving a biological sample. Furthermore, sample collection and preservation are simplified, which decreases the likelihood that even an unskilled user will err when collecting and preserving a biological sample. As an illustrative example of the foregoing, biological sample collection kits disclosed herein include at least a two-piece sample collection and preservation system. A first portion includes a sample collection vessel or vial, which can be detachably associated with a funnel. When used, the funnel acts to guide the receipt of a sample from a user into the sample collection chamber of the collection vessel or vial. The funnel can also make it easier for a user to engage the sample collection vessel and deposit a biological sample into the sample collection chamber. After depositing the requisite amount of biological sample, a user can remove the funnel (if used) and associate the second portion of the two-piece sample preservation system—e.g., a sealing cap associated with a reagent chamber—with sample collection vessel. The reagent chamber has been pre-filled with a predetermined amount of sample preservation reagent(s), and as the sealing cap is drawn down to seal the received biological sample within the sample collection chamber, the reagent(s) are released from the reagent chamber and into the sample collection chamber, mixing with and preserving the received biological sample.

As described in more detail below, the reagent chamber can be opened to release reagents into the sample collection chamber in a plurality of ways. In some embodiments, the reagent chamber is associated with a selectively movable sleeve valve, and when the sealing cap and reagent chamber are associated with the sample collection vessel, the selectively movable sleeve valve opens (e.g., by undergoing a physical rearrangement), permitting previously obstructed fluid vent(s) to communicate fluid between the reagent compartment and the sample collection chamber. Reagent(s) in the reagent compartment can be released into the sample collection chamber through the fluid vent(s). In some embodiments, the opening of the selectively movable sleeve valve is reversible. For example, disassociating the sealing cap from the sample collection vessel can cause the selectively movable sleeve valve to close.

As can be appreciated from the foregoing, in addition to alternative and/or additional embodiments provided herein, the systems, kits, and methods of the present disclosure can be used by skilled or unskilled individuals with reduced likelihood of error associated with collecting and at least initially preserving a biological sample. Accordingly, implementations of the present disclosure can reduce the cost associated with procuring biological samples for diagnostic, scientific, or other purposes and can increase the geographic reach of potential sample collection areas without the need of establishing the necessary infrastructure (e.g., controlled environments conducive to sample collection and preservation, skilled personnel to physically collect, transport, and/or preserve the biological samples, etc.).

As used herein, the term "biological sample" can include any cell, tissue, or secretory fluid (whether host or pathogen related) that can be used for diagnostic, prognostic, genetic, or other scientific analysis. This can include, for example, a human cell sample such as skin. It can also include a non-human cell sample that includes any of a bacterium, virus, protozoa, fungus, parasite, and/or other prokaryotic or eukaryotic symbiont, pathogen, or environmental organism. The term "biological sample" is also understood to include fluid samples such as blood, urine, saliva, and cerebrospinal fluid and extends to other biological samples including, for example, mucus from the nasopharyngeal region and the lower respiratory tract (i.e., sputum). Examples of biological samples include, but are not limited to, saliva, sputum, spit, blood, perspiratory fluid, sweat, pus, tear, mucosal excretion, vomit, urine, stool, semen, vaginal fluids, other type of bodily fluid, cell-free samples, cheek swabs, swabs of a different bodily part, homogenous samples, heterogeneous samples, tumor samples, plasma, or serum samples.

As used herein, the "probative component" of the biological sample refers generally to any protein, nucleic acid, surface moiety, or other compound that can be isolated from the biological sample. Preferably, the probative component is or includes nucleic acid, more preferably DNA. In a preferred embodiment, the biological sample is or includes saliva, which presumptively contains a preferable probative component in the form of the user's genetic material (e.g., DNA and RNA).

A Multi-Part Self-Contained Sample Collection System/Kit

In one embodiment, a biological sample is collected, preserved, and stored in a collection vessel as part of a multi-piece, self-contained sample collection system or kit. A first piece of the system or kit includes a sample collection vessel, a second piece includes a sample collection funnel, which may be packaged separately from or removably connected to the sample collection vessel, and a third piece includes a sealing cap having a selectively movable sleeve valve comprised of an inner vessel and an outer sleeve and a reagent chamber disposed within or integrated with the sealing cap. The sealing cap is configured to associate with the sample collection vessel, to dispense sample preservation reagents into the sample collection vessel through the selectively movable sleeve valve, and to seal the contents therein.

For example, FIG. 1 illustrates an exploded view of a three-dimensional model depicting a biological sample collection system or kit 100. The system 100 includes a sample collection vessel 102 and optionally, a funnel (not shown), which can be associated with a top portion of the sample collection vessel 102 and in fluid communication with a sample collection chamber 103 of the sample collection vessel 102. The biological sample collection system 100 can also include a selectively movable sleeve valve 104 comprised of an inner vessel 106 and an outer sleeve 108 associated with a sealing cap 110 that has a reagent chamber 111 disposed within or integrated with the sealing cap 110. The sealing cap 110—together with the selectively movable sleeve valve 104—can be sized and shaped to associate with a top portion of the sample collection vessel 102, fitting over and sealing an opening of the sample collection chamber 103. The sealing cap 110 may also be referred to as an outer cap. For example, the sealing cap 110 can be removably engaged with the sample collection vessel 102 by any suitable manners, such as by screw threads, snap fit, frictional fit, etc. Examples of mechanisms for removably engaging the sealing cap 110 with the sample collection vessel 102 include, but are not limited to, complementary threading, form-fitting pairs, interference fitting, hooks and loops, latches, screws, staples, clips, clamps, prongs, rings, brads, rubber bands, rivets, grommets, pins, ties, snaps, velcro, adhesives, tapes, vacuum, seals, or any combination thereof.

In various embodiments, the inner vessel 106 and the outer sleeve 108 may be coupled to each other using any suitable methods, such as interference fit, press fit, friction fit, compression fit, snap fit, mechanical features, chemical bond, material interaction (e.g. swelling), solvent bond, interference fit and snap fit, interference fit and mechanical features, interference fit and chemical bond, interference fit and solvent bond, interference fit and material interaction, compression fit and snap fit, compression fit and mechanical features, compression fit and chemical bond, compression fit and solvent bond, compression fit and material interaction, interference fit and snap fit and chemical bond, interference fit and snap fit and solvent bond, interference fit and snap fit and material interaction, interference fit and mechanical features and chemical bond, interference fit and mechanical features and solvent bond, interference fit and mechanical features and material interaction, or any suitable combination thereof.

In some embodiments, the reagent(s) within the reagent chamber 111 includes a preservation or buffering solution that protects the integrity of the probative component of the biological sample prior to purification or testing. Preservation reagents are typically chemical solutions and may contain one or more salts (e.g., NaCl, KCl, $Na_2HPO_4$, $KH_2PO_4$, or similar, and which may, in some implementations, be combined as a phosphate buffered saline solution, as known in the art), lysing agents (e.g., detergents such as Triton X-100 or similar), chelating agents (e.g., ethylenediaminetetraacetic acid (EDTA), ethylene glycol-bis(β-aminoethyl ether)-N,N,N',N'-tetraacetic acid (EGTA), or similar), distilled water, or other reagents known in the art. In one or more embodiments, the reagent or buffering solution stabilizes at least one probative component within the sample (e.g., nucleic acids, such as DNA and RNA, protein, etc., and combinations thereof) during transfer, transportation, and/or storage at a laboratory, clinic, or other destination. In some embodiments, the sample can be stored, at or below room temperature after the preservation solution is added, for weeks or months without significant loss of the probative component. That is, the sample can still be utilized for diagnostic, genetic, epidemiologic, or other purposes for which it was collected after storage for weeks or months in the preservation solution.

With continued reference to FIG. 1, the sealing cap 110 and a saliva funnel (not shown) can each independently attach to the sample collection vessel 102 using a connection mechanism. The connection mechanism can include, for example, threads, snap or press fit connections, tongue and groove members, bayonet connection, or other interlocking or mechanically coupling mechanisms. For example, a funnel can be first attached to the sample collection vessel 102 via complementary connection mechanisms (e.g., complementary threads; not shown). After facilitating receipt of a biological sample from a user, the funnel can be removed by reversing the complementary connection mechanism (e.g., unscrewing the funnel; not shown), and a sealing cap 110 can be secured to the sample collection vessel 102 using a same or similar complementary connection mechanism, as shown in FIG. 2. That is, the sealing cap 110 can include connection members 126 (e.g., threads) located on an inner circumferential wall of the sealing cap 110 that are complementary to and work in conjunction with the connection members 124 (e.g., complementary threads) disposed on an exterior surface of the sample collection vessel 102.

In some embodiments, the connection mechanism between the funnel and sample collection vessel 102 is different than the connection mechanism between the sealing cap and the sample collection vessel 102. For example, the funnel may be press fit or snap fit onto the sample collection vessel 102, whereas the sealing cap is rotationally secured through engagement of complementary threads 124 and 126 located on an exterior portion of the sample collection vessel 102 and an interior portion of the sealing cap 110 or vice versa. Regardless of the attachment mechanism used, a sample preservation reagent can be introduced into the sample collection chamber 103 of the sample collection vessel 102 and mixed with the deposited biological sample as a result of the sealing cap 110 being attached to the sample collection vessel 102. As provided earlier, this can be due to the selectively movable sleeve valve 104 opening and allowing reagent(s) to be released through fluid vents 130 defined by the selectively movable sleeve valve 104 and into the sample collection chamber 103.

In an embodiment, the sealing cap 110 receives a measure of reagents into the reagent chamber 111, and as shown by the cross-sectional views of the assembled biological sample collection system 100A in FIG. 2, a selectively movable sleeve valve 104 (in a closed configuration) is associated with the sealing cap 110, sealing the reagents within the sealing cap 110. The inner vessel 106 is snap-fittingly received into the sealing cap 110 creating a fluid-tight connection. As illustrated, the inner vessel includes a retaining ring 114 into which a protrusion 112 of the interior sidewall of the sealing cap 110 inserts to stabilize the inner vessel 106. In some embodiments, the interaction between the protrusion 112 and the retaining ring 114 creates the fluid-tight connection between the sealing cap 110 and the inner vessel 106. Additionally, or alternatively, an upper collar 109 of the inner vessel extends into the reagent chamber 111 and associates there via an interference fit, creating a fluid-tight connection between the interior sidewall of the reagent chamber 111 and the exterior sidewall of the upper collar 109 of the inner vessel 106.

As further illustrated by FIG. 2, the inner vessel 106 includes a reagent retention chamber 107 in fluid communication with the reagent chamber 111. The inner vessel 106 may be securely engaged with the sealing cap 110 such as by adhesion, snap fit, compression fit or another more permanent engagement manner. The inner vessel 106 includes fluid vents 130, through which reagent may be transferred from the reagent chamber 111 to the sample collection chamber 103. However, in FIG. 2, any reagent within the reagent chamber 111 would be retained, owing to the closed configuration of the selectively movable sleeve valve 104. That is, as illustrated in FIG. 2, the fluid vents 130 are obstructed by an outer sleeve 108 of the selectively movable sleeve valve 104. An interior sidewall 122 of the outer sleeve 108 defines an aperture into which the inner vessel 106 extends, and the interaction between the interior sidewall 122 of the outer sleeve 108 and the exterior sidewall 118 of the inner vessel 106 creates a fluid-tight connection—at least at and/or around fluid vents 130. The fluid-tight connection between the outer sleeve 108 and the inner vessel 106 prevents the reagents within the reagent chamber 111 from passing into the reagent retention chamber 107 and out through fluid vents 130. Fluid vents 130 may also be used to provide a path for air to enter into a reservoir associated with the reagent retention chamber 107 and the reagent chamber 111. The entering air balances the air pressure inside the reservoir with the external air pressure, allowing the reagent to flow, by gravitational force, from the reservoir into the sample collection chamber 103 when the fluid vents 130 are opened.

As also shown in FIG. 2, the outer sleeve 108 associates with sealing cap 110 and the opening of the sample collection chamber 103. A guide member 120 of the outer sleeve 108 protrudes away from the body of the outer sleeve 108 and extends into a guide channel 116 formed by the interior surface of the sealing cap 110. The guide member 120 acts, in some embodiments, to retain the outer sleeve 108 in association with the sealing cap 110. The outer sleeve 108 additionally includes a lower collar 132 that associates with the interior sidewall of the sample collection chamber 103. In some embodiments, the lower collar 132 associates with the sample collection chamber 103 via an interference fit, which can serve to stabilize the selectively movable sleeve valve 104, the sealing cap 110, and the sample collection vessel 102. In some embodiments, the interference fit between the outer sleeve 108 and the sample collection chamber 103 is a liquid-tight fit. Some embodiments of the outer sleeve 108 may not include a guide member 120, instead relaying on the raised ridges 121 of the inner vessel 106 to form a liquid-tight seal with the interior sidewall 122.

As the complementary threads 124, 126 between the sealing cap 110 and the sample collection vessel 102 are inter-engaged and the sealing cap 110 is advanced towards the sample collection vessel 102, the inner vessel 106—which is coupled to the sealing cap 110—is similarly advanced. As shown in FIG. 3, the inner vessel 106 is pushed through the aperture defined by the outer sleeve 108, positioning the selectively movable sleeve valve 104 in an open configuration. In the open configuration depicted in FIG. 3, the fluid vents 130 are positioned below—and now unobstructed by—the lower terminal edge of the outer sleeve 108. Reagent(s) within the reagent chamber 111 can now freely pass through the reagent retention chamber 107 of the inner vessel 106, through the fluid vents 130, and into the sample collection chamber 103.

In the embodiment shown in FIG. 3, the outer sleeve 108 does not move relative to the sample collection vessel 102. The sealing cap 110 and the associated inner vessel 106 advance relative to the outer sleeve 108 and the sample collection vessel 102. In some embodiments, and as shown in FIG. 3, the body of the outer sleeve 108 above the lower collar 132 has a larger diameter than the lower collar 132, and this larger diameter body does not fit within the opening of the sample collection chamber 103. Instead, it abuts and is impeded by the upper rim of the sample collection chamber 103 that defines the opening thereof. This prevents the outer sleeve 108 from advancing along with the inner vessel 106 and the sealing cap 110 toward sample collection vessel 102. The resistive force impeding progress of the outer sleeve 108 is greater than the frictional force between the inner vessel 106 and the outer sleeve 108, and the torque (or other force) applied to the sealing cap 110 to associate the sealing cap 110 with the sample collection vessel 102 is greater than the frictional force between the inner vessel 106 and the outer sleeve 108. Accordingly, the selectively movable sleeve valve 104 undergoes a conformational change where the inner vessel 106 advances through the outer sleeve 108, revealing the fluid vents 130 (as shown in FIG. 3).

As shown in FIGS. 2 and 3, the guide member 120 moves along the guide channel 116 as the sealing cap 110 threadedly secures to the sample collection vessel 102.

In some embodiments, the distance required to open the selectively movable sleeve valve 104 is proportional to the distance required to at least partially unobstruct the fluid vents 130. This distance may be the same or less than the distance between the terminal edge of the sealing cap 110 and the stop member 128 disposed on the external surface of the sample collection vessel 102 when the connection members 124, 126 thereof initially engage.

Although there are only two fluid vents 130 illustrated in FIGS. 2 and 3, it should be appreciated that in some embodiments there can be more or fewer fluid vents 130. For example, a second pair of fluid vents 130 (not shown) can be defined on the opposite side of the inner vessel 106. In some embodiments, the fluid vents 130 can be a different shape and/or the selectively movable sleeve valve 104 may operate differently than illustrated in FIGS. 2 and 3. For example, the outer sleeve 108 may define an open-ended chamber into which the inner vessel 106 is inserted. However, instead of being pushed through an open bottom of the outer sleeve 108, depression of the inner vessel 106 (e.g., by association of the sealing cap 110 with the sample collection vessel 102) can align fluid vents 130 defined by the inner vessel 106 with analogous fluid vents 130 defined by the outer sleeve 108, thereby providing a through hole between the sample collection chamber 103, the reagent retention chamber 107 of the inner vessel, and the reagent chamber 111 of the sealing cap 110.

Referring now to FIG. 4, the sealing cap 110 may additionally include a plurality of external ridges 125. The external ridges 125 can facilitate a user to better grip the sealing cap 110 while positioning the sealing cap 110 over the sample collection vessel 102. Additionally, or alternatively, the external ridges 125 can be used to rotate and close the sealing cap 110 onto the sample collection vessel 102. In some embodiments, ridges 125 may beneficially enable the user to more forcefully turn the sealing cap 110, and the external ridges 125 can provide the user with a better grip during that process. Ridges 125 can also facilitate retraction and/or closure of the selectively movable sleeve valve 104 and/or removal of the sealing cap 110 at the laboratory when accessing the biological sample, such as manually or by an automated removal mechanism.

Figure 5A:
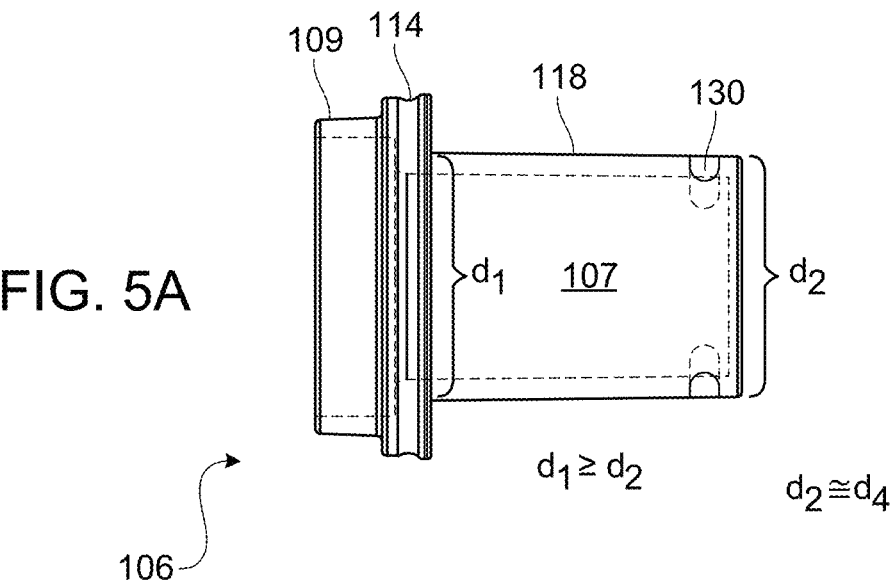
FIG. 5A illustrates an elevation view of the inner vessel of the sample collection system depicted in FIG. 4.

Referring now to FIG. 5A, the inner vessel 106 includes one or more tapered regions, which can, among other things, help fit the inner vessel 106 into the sealing cap 110 and into the aperture 134 of the outer sleeve 108. For example, the inner vessel 106 can include an upper collar 109 that is sized and shaped to fit within the sealing cap 110 and to create a fluid-tight seal therewith (as described above). As shown, the upper collar 109 can be tapered with a larger diameter adjacent to the retaining ring 114 and a smaller diameter moving away from the retaining ring 114 toward the terminal end thereof. The smaller diameter end of the upper collar 109 can be a smaller diameter than the diameter of the reagent chamber 111, which can beneficially allow the inner vessel 106 to be more easily associated with the sealing cap 110. As the diameter of the upper collar 109 increases when moving toward the retaining ring 114, it forms an interference fit with the associated reagent chamber 111, which can additionally be a fluid-tight fit.

The inner vessel 106 additionally includes a tapered exterior sidewall 118 that is sized and shaped to fit within the aperture 134 of the outer sleeve 108. As illustrated, the exterior sidewall 118 can taper from a first diameter d1 to a second diameter d2, where d1>d2.

Figure 6A:
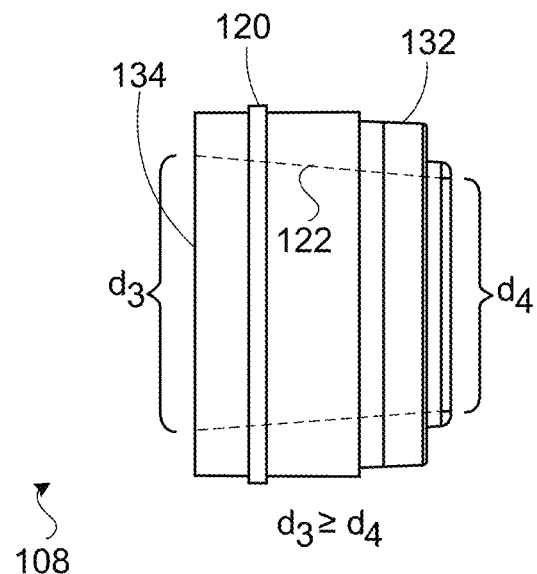
FIG. 6A illustrates an elevation view of an outer sleeve of a sample collection system.
Figure 6B:
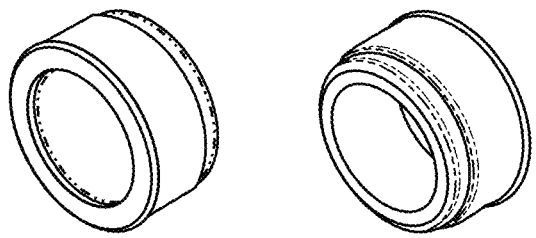
FIG. 6B illustrates perspective views of a three-dimensional model of an outer sleeve of a sample collection system.

As shown in FIG. 6A, the interior sidewall 122 defining the aperture 134 of the outer sleeve 108 can additionally be tapered. For example, as shown in FIG. 6A, the interior sidewall 122 can be tapered from a proximate end having a diameter d3 to a distal end having a diameter d4, where d3>d4. The distal end diameter d4 can be, in some embodiments, about the same size as the second diameter d2 (shown in FIG. 5A) of the inner vessel 106 such that when the inner vessel 106 is associated with the outer sleeve 108, an interference fit is created, which can additionally be a fluid-tight fit. FIG. 6B illustrates a front perspective view and a rear perspective view of the outer sleeve 108, according to one embodiment.

In some embodiments, the exterior sidewall 118 of the inner vessel 106 is tapered to the same degree as the interior sidewall 122 of the outer sleeve 108. In such an embodiment, the interior sidewall 122 may associate directly with the exterior sidewall 118 along its entire length and forming an interference fit therebetween.

In some embodiments, the exterior sidewall 118 of the inner vessel 106 is tapered to a different degree than the interior sidewall 122 of the outer sleeve 108. For example, the interior sidewall 122 can be tapered more aggressively than the exterior sidewall 118 such that d1<d3. In such an embodiment, a gap would form between the outer sleeve 108 and the inner vessel 106 at the proximate end of the outer sleeve 108. In some embodiments, the length of the aperture 134 is shorter than the length of the exterior sidewall 118, and only a portion of the exterior sidewall 118 associates with the aperture 134. Accordingly, d1 may be roughly equivalent to d3, and the degree of taper of the exterior sidewall 118 would still be less than the degree of taper of the interior sidewall 122 defining aperture 134. In such an embodiment, a gap would form between the outer sleeve 108 and the inner vessel 106 at the proximate end of the outer sleeve 108, similar to that described above.

Figure 5B:
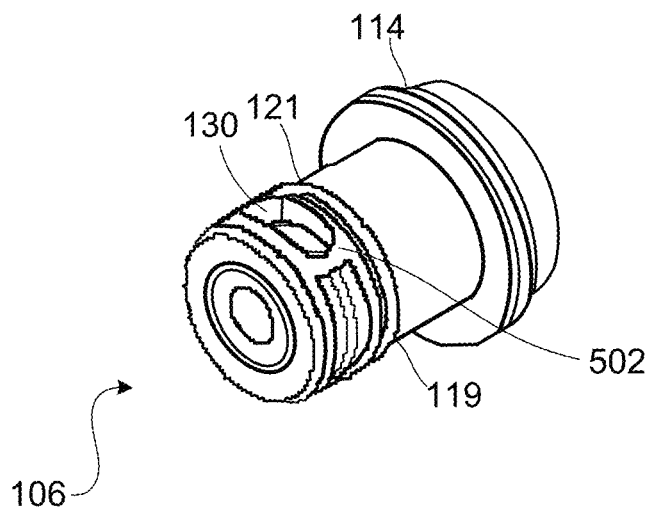

In some embodiments, the exterior sidewall 118 of the inner vessel 106 is lined with one or more raised surface areas. FIG. 5B illustrates a perspective view of an inner vessel 106 with a raised surface area 119, according to an embodiment. For example, the raised surface area 119 is formed on the outer surface of the cylindrical body of the inner vessel 106. The raised surface area 119 includes or provides one or more raised ridges 121 lined around the exterior sidewall 118 to partially or completely cover the circumference of the inner vessel 106 and also forms a surface ring 502 on the cylindrical surface of the inner vessel 106. The surface ring 502 surrounds a fluid vent 130, which may be located at the circumferential surface of the cylindrical body of the inner vessel 106. The raised ridges 121 may be individually configured at a range of depths and widths. In the embodiment illustrated in FIG. 5C, the raised surface area 119 includes three raised ridges (best shown in FIG. 5C), 121a, 121b, and 121c (which may be collectively referred to as 121). FIG. 5E shows an embodiment where the raised surface area 119 takes the form of a sleeve band 503 coupled to the inner vessel 106. This sleeve band 503 may be manufactured using a plurality of materials including, but not limited to, polymeric materials such as thermoplastics and its variants (e.g., thermoplastic elastomers, thermoplastic vulacnizates), rubber, including nitrile, silicone, polyurethane, PTFE, and neoprene, other plastics, ceramics, fiber materials, or any other material with suitable elasticity, rigidity or other suitable properties and characteristics. In embodiments in which the raised surface area 119 comprises multiple raised ridges 121, the raised ridges 121 may be equally spaced along the exterior sidewall 118 or may be spaced varying distances apart over the exterior sidewall 118, for example, the embodiment illustrated in FIG. 5B. There may be raised ridges 121 above and below the fluid vents 130 to create raised surface areas.

In some embodiments, the raised surface area 119 includes a raised surface surrounding the fluid vents 130 of the inner vessel to prevent preservation fluid from filling up the space between the upper ridge 121a and the lower ridge 121b of the inner vessel, thus reducing the surface area needing to be sealed. In such an embodiment, the raised surface reduces the surface area needed to form a fluid-tight seal. As described above, the inner vessel 106 may be designed as a hollow or a semi-hollow vessel to allow the transfer of fluid from the reagent chamber 111 into the sample collection chamber 103.

Figure 5C:
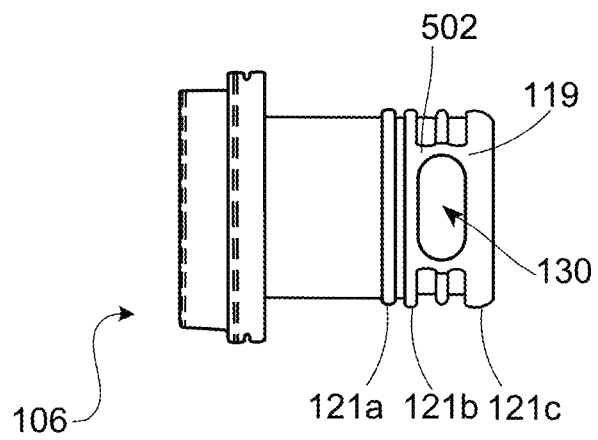

In the illustrated embodiment, the raised surface area 119 lines the inner vessel 106 near the face of the inner vessel 106 which inserts into the outer sleeve 108. However, in alternate embodiments, the raised surface area 119 may be adjusted to line the inner vessel closer to the retaining ring 114. When the inner vessel 106 is inserted into the outer sleeve 108, for example in a closed configuration, each of the raised ridges 121 are placed in contact with the interior sidewall of the outer sleeve 108 to provide a friction fit for better engagement between the inner vessel 106 and the outer sleeve 108. The surface ring 502 of the raised surface area 119, which surrounds the fluid vent 130, frictionally engages with inner sidewall 122 of the outer sleeve 108 to provide a fluid-tight seal at the interface of the inner vessel 106 and outer sleeve 108 and to prevent preservation reagent from seeping through the space between the exterior sidewall 118 of the inner vessel 106 and the inner sidewall 122 of the outer sleeve 108 into any open space. FIG. 5C illustrates a side view of an inner vessel 106 comprising the raised surface area 119, according to an embodiment. In the illustrated embodiment, the raised surface area 119 includes a surface ring 502 coupled to the two raised ridges 121a and 121b closest to the face of the inner vessel 106 which is oriented towards the outer sleeve 108.

FIG. 5D illustrates additional front perspective and rear perspective views of an inner vessel 106 lined with a raised surface area 119, according to an embodiment. FIGS. 5E and 5F are two cross-sectional views of the inner vessel 106 with raised surface area 119, according to an embodiment. FIG. 5F is rotated 90 degrees compared to FIG. 5E so that the fluid vents 130 are shown as facing up and down instead of sideways. FIG. 5G illustrates enlarged views of detail E 550 of FIG. 5E, which shows the raised surface area 119 of the inner vessel 106 with recesses 560 that form the raised ridges 121 in the raised surface area 119. The recesses 560 enhance the frictional fit of the inner vessel 106 with the outer sleeve 108. The raised ridge 121a is positioned on the end of the inner vessel 106 that engages with the outer sleeve 108 (not shown in FIGS. 5E-5G) and the raised ridge 121b is positioned at the end of the inner vessel 106 that engages with the sealing cap 110. FIG. 5G illustrates enlarged views of detail E 550 of FIG. 5E, showing two alternative embodiments. For the embodiment on the right, the raised surface area 119 may include an additional recess 570 to further enhance frictional fit.

Figure 5H:
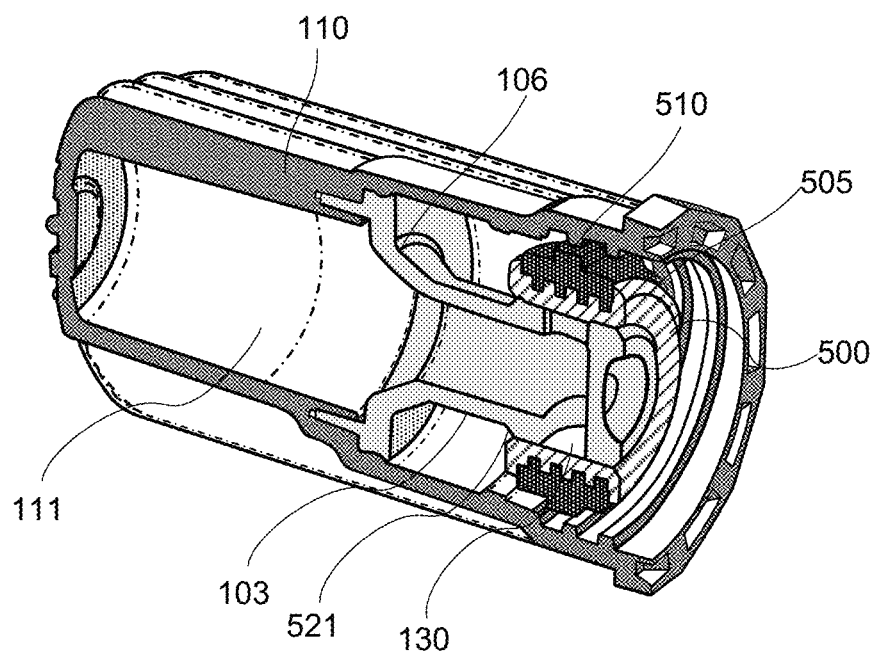
FIGS. 5H-5M illustrate various views of various components of a sample collection system, including sealing cap, inner vessel, and outer sleeve comprised of an inner and outer band.

FIGS. 5H-5M illustrate embodiments that show additional or alternative features of different possible variations of a sample collection system. The sample collection system may include a sealing cap 110, an inner vessel 106 that is securely engaged with a sealing cap 110, an outer sleeve 500 that is frictionally engaged with the raised surface area 521 of the inner vessel 106, and a sample collection vessel, for example, the sample collection vessel 102. FIGS. 5H through 5K show various components of a sealing cap 110. An example of an outer sleeve 500 includes dual layers and is configured to slide over the fluid vents 130 of an inner vessel 106. FIG. 5H illustrates a perspective view of a cross-section of the sealing cap 110 having an inner vessel 106 securely coupled to the sealing cap 110 and with an outer sleeve 500 movably coupled to the inner vessel 106, which surrounds a portion of the inner vessel 106. The outer sleeve 500 includes two layers: an inner band 505 and an outer band 510. The inner band 505 may be referred to as a sealant band of an outer sleeve 500 and the outer band 510 may be referred to as a backing band of the outer sleeve 500. In one embodiment, the raised surface area 521 may be functionally consistent with the above description of the raised surface area 119 and may also take the shape shown in FIGS. 5E through 5G. As described above, the inner vessel 106 includes fluid vents 130 through which preservation reagent flows into the sample collection chamber 103. In a resting state, in which the inner vessel 106 is unengaged with the sample collection vessel 102, the inner band 505 of the outer sleeve 500 frictionally engages with the raised surface area 521 of the inner vessel 106 and covers the fluid vents 130 to provide a fluid-tight seal around the fluid vents 130. The fluid-tight seal prevents preservation reagent from seeping through the space between the raised surface area 521 of the exterior sidewall 118 of the inner vessel 106 and the interior sidewall 122 defining the aperture of the outer sleeve 500. Each of the inner band 505 and the outer band 510 may be manufactured using a plurality of materials including, but not limited to, polymeric materials such as thermoplastics and their variants (e.g., thermoplastic elastomers, thermoplastic vulcanizates), rubber, including nitrile, silicone, polypropylene, polyurethane, PTFE, and neoprene, other plastics, ceramics, fiber materials, or any other material with suitable elasticity and rigidity or other suitable properties and characteristics. The inner band 505 and the outer band 510 may be made from different materials with different physical properties. For example, in one embodiment, the inner band 505 may be made from a first material that is softer than the material of the outer band 510. The softer inner band 505 may provide a better sealing effect to the inner vessel 106 while the stiffer outer band 510 may provide sufficient mechanical strength for interacting with other components to open the fluid vent 130 in a manner that will be discussed below. In one embodiment, the interior diameter of the inner band 505 is smaller than the outer diameter of the raised surface area 521 of the inner vessel 106 so that the inner band 505 is compressed between the outer band 510 and the raised surface area 521. When the inner band 505 frictionally engages with the raised surface area 521, the compression between the outer band 510 and the raised surface area 521 forms a fluid-tight seal between the inner vessel 106 and the outer sleeve 500.

Figure 5I:
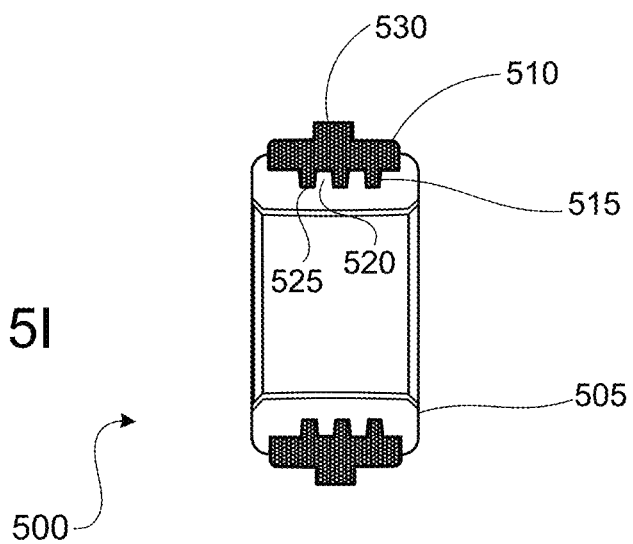

FIG. 5I is a cross-sectional view of an embodiment of outer sleeve 500 that includes a inner band 505 (not shaded) and a outer band 510 (shaded), in accordance with an embodiment. The exterior face of the inner band 505 may take the form of a ridged surface configured to couple with a complimentary ridged interior face of the outer band 510 at the backing band-sealant band interface 515. The exterior face of the inner band 505 includes multiple locking ridges 520 and the interior face of the outer band 510 includes a complementary set of locking ridges 525 that enable the inner band 505 and the outer band 510 to interlock and form an outer sleeve 500. At the backing band-sealant band interface 515, the outer band 510 and the inner band 505 may be coupled by various methods such as frictionally fit, chemically bonded, overmolded, induction welded, thermally welded or any other suitable technique or combination of techniques, to form an outer sleeve 500. The raised ridges of the inner band 505 interlock with the complementary ridges of the outer band 510 to provide a mechanical means of holding the sealant band and the backing band together. The ridged surface of the inner band 505 and the corresponding complementary ridges of the outer band 510 provide additional surface area to improve the coupling properties between the outer band 510 and the inner band 505. In some embodiments, additional mechanical features, such as the ridges of the inner band 505 and the outer band 510 described above, may contribute to the coupling properties of the materials of the inner band 505 and the outer band 510. For example, additional features contributing to the coupling properties include, but are not limited to, fasteners, snap fits, tabs, increased contact surface area, interference fits or other means. The inner band 505 and the outer band 510 may also be coupled by frictional fit, chemical bonding, solvent bonding, overmolding, induction welding, thermal welding, tapes, adhesives, etc. to generate an integrated outer sleeve 500. The raised ridges 520 of the inner band 505 and the complementary ridges 525 of the outer band 510 may be equally spaced or may be spaced at varying distances apart. The outer sleeve 500 may also include an exterior ridge 530 that allows a component (e.g., the upper rim of the sample collection vessel 102) to push the outer sleeve 500.

In various embodiments, the outer sleeve 108 may take different forms and include one or more components. In one embodiment, the outer sleeve 500 shown in FIG. 5I is an example of outer sleeve 108. In another embodiment, the outer sleeve may also be formed of a single material. In one embodiment, the outer sleeve is symmetrical to allow the sleeve to be coupled with the inner vessel 106 in any orientation. In one embodiment, the outer sleeve is asymmetrical. In one embodiment, the outer sleeve may also have raised surface areas or ridges in the interior surface to enhance the friction between the inner vessel 106 and the outer sleeve. Other combinations of features mentioned are also possible. For the embodiment shown in FIG. 5I, the inner band 505 and outer band 510 may be coupled using overmolding, interference fit, frictional fit, fasteners, mechanical features, snap fits, press fit, tabs, adhesives, tapes, solvent bonding, chemical bonding, UV bonding, induction welding (ultrasonic, vibration, friction), thermal welding, overmolding and mechanical features, frictional fit and mechanical features, adhesive and mechanical features, chemical bonding and mechanical features, friction welding and mechanical features, or another suitable combination of interface joining methods.

Figure 5J:
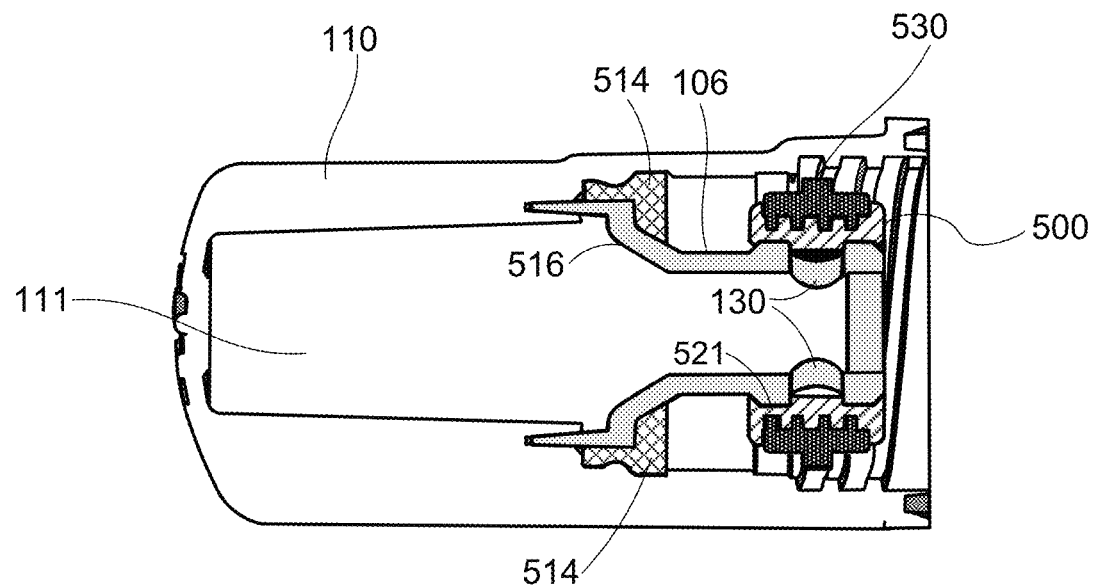

FIG. 5J illustrates a side view of a cross-section of an inner vessel 106 with an outer sleeve 500 in a closed position. The outer sleeve 500 can be frictionally engaged with the inner vessel 106. The friction permits the outer sleeve 500 to be slidable translationally relative to the longitudinal body of the inner vessel 106 between a closed position (shown in FIG. 5J) and an open position (shown in FIG. 5K). The outer sleeve 500 at the closed position covers the fluid vents 130. The outer sleeve 500 at the open position is displaced from the fluid vents 130, thereby opening the fluid vents 130. In the closed position illustrated in FIG. 5J, the inner band 505 of the outer sleeve 500 has a first surface area that is in contact with the raised surface area 521 of the inner vessel 106 on either side of the fluid vents 130. The surface area contact forms a fluid-tight seal that prevents preservation fluid from flowing out of the fluid vents 130. In some embodiments, the inner band 505 interacts with preservation fluid stored in the inner vessel 106 to improve the performance of the fluid-tight seal formed around the fluid vents. For example, the inner band 505 may be designed using material that swells upon contact with a preservation fluid. The swollen inner band 505 increases compression of the sealant band against the fluid vents 130 and raised surface area 521 adjacent to the fluid vents 130, thereby improving the effectiveness of the fluid-tight seal. As another example, the inner band 505 may, upon contact with a preservation fluid, undergo a chemical reaction to create a fluid-tight seal or to improve upon the performance of an existing fluid-tight seal.

FIG. 5J also shows an additional or alternative feature in coupling the inner vessel 106 and the sealing cap 110. In this example, the inner vessel 106 includes a cap band 514 (represented as having crosshatched pattern) and an inner layer 516 (shown as shaded). The cap band 514 and the inner layer 516 can be made of different materials. The cap band 514 may be formed of a softer and more elastic material such as thermoplastics and their variants (e.g., thermoplastic elastomers, thermoplastic vulcanizates), silicone, etc. The cap band 514 acts as a sealant layer, being compressed between the inner layer 516 of the inner vessel 106 and the inside wall of the sealing cap 110 to form a fluid-tight seal. A press fit between the inner layer 516 of the inner vessel 106 and the sealing cap 110 forms a liquid-tight seal. The inner layer 516 may be formed of a stiffer material such as any suitable polymer, including a thermoplastic polymer such as polypropylene.

Both the inner layer 516 and cap band 514 of the inner vessel 106 can take many forms and engage with the sealing cap 110 by any suitable methods such as interference fit (press fit, friction fit), compression fit, snap fit, mechanical features, chemical bonding, material interaction (e.g. swelling), solvent bonding, interference fit with snap fit, interference fit with mechanical features, interference fit with chemical bonding, interference fit with solvent bonding, interference fit with material interaction, compression fit with snap fit, compression fit with mechanical features, compression fit with chemical bonding, compression fit with solvent bonding, compression fit with material interaction, interference fit with snap fit with chemical bonding, interference fit with snap fit with solvent bonding, interference fit with snap fit with material interaction, interference fit with mechanical features with chemical bonding, interference fit with mechanical features with solvent bonding, interference fit with mechanical features with material interaction, any combination thereof, or any other suitable methods not explicitly described.

Figure 5K:
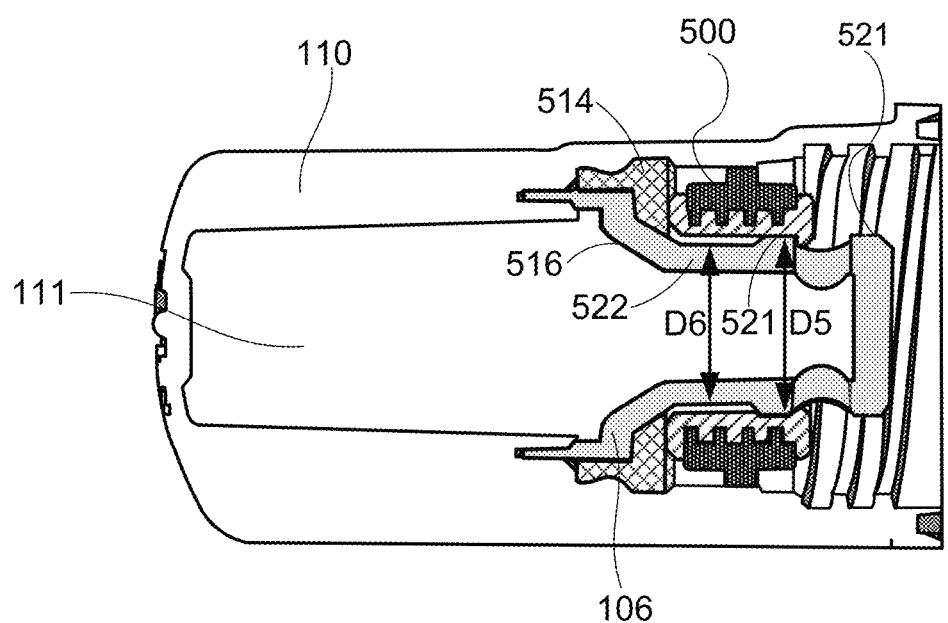

In the open position illustrated in FIG. 5K, the outer sleeve 500 is moved to another location that is only partially in contact with the raised surface area 521 of the inner vessel 106. In some variations, the outer sleeve 500 may also be distanced from the raised surface area 521. The outer sleeve 500 is moved to a thinner body portion 522 of the inner vessel 106. The thinner body portion 522 has a smaller outer diameter than that of the portion at the raised surface area 521. Hence, the outer sleeve 500 is less compressed at the thinner body portion 522. As the inner vessel 106 slides translationally relative to the outer sleeve 500, or alternatively as the outer sleeve 500 slides translationally relative to the inner vessel 106, the amount of surface area of the outer sleeve 500 being in contact with the raised surface area 521 of the inner vessel 106 decreases, thereby reducing the amount of force required to slide the inner vessel 106 translationally as the fluid vent 130 is exposed. For example, in one embodiment, the outer diameter D5 of the inner vessel 106 is larger at a first position where the outer sleeve 500 resides in the closed position (shown in FIG. 5J) than the outer diameter D6 of the inner vessel 106 at a second position where the outer sleeve 500 resides in the open position (shown in FIG. 5K). The smaller diameter D6 reduces the area of compression of the inner band 505 between the outer band 510 and the inner vessel 106, thereby reducing the frictional force between the inner band 505 and the inner vessel 106. Hence, after a user applies initial forces to surpass the friction between the inner band 505 and the inner vessel 106 in the closed position, the friction is further reduced as the inner vessel 106 tapers thinner (diameter D5 to diameter D6), thereby reducing the amount of force needed to slide the outer sleeve 500 translationally as the fluid vents 130 are being opened.

Figure 5L:
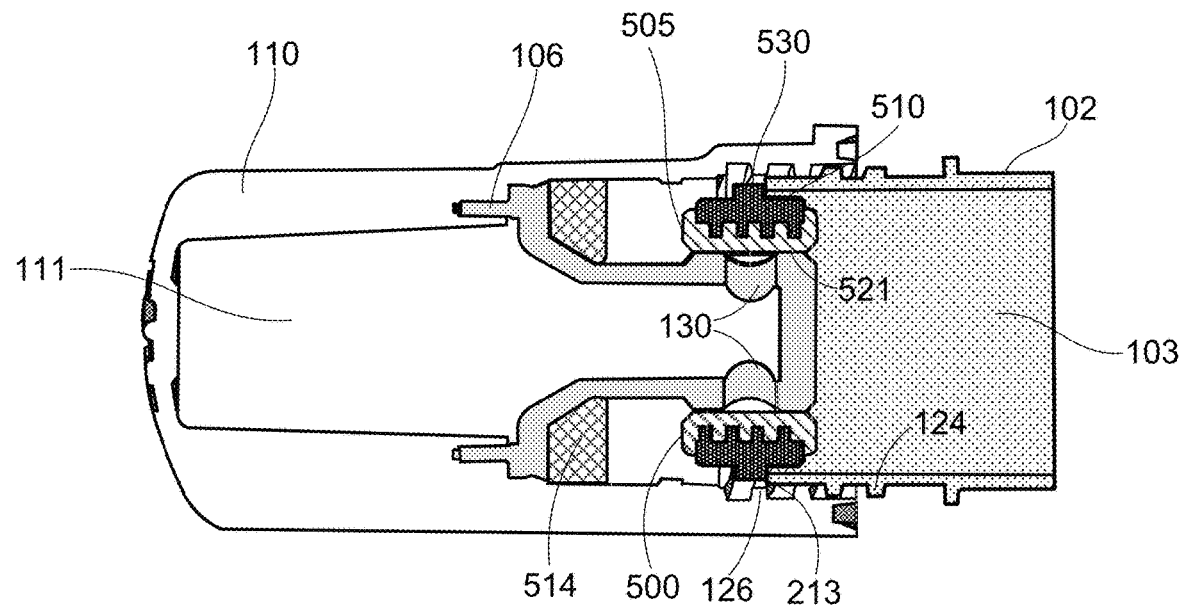
Figure 5M:
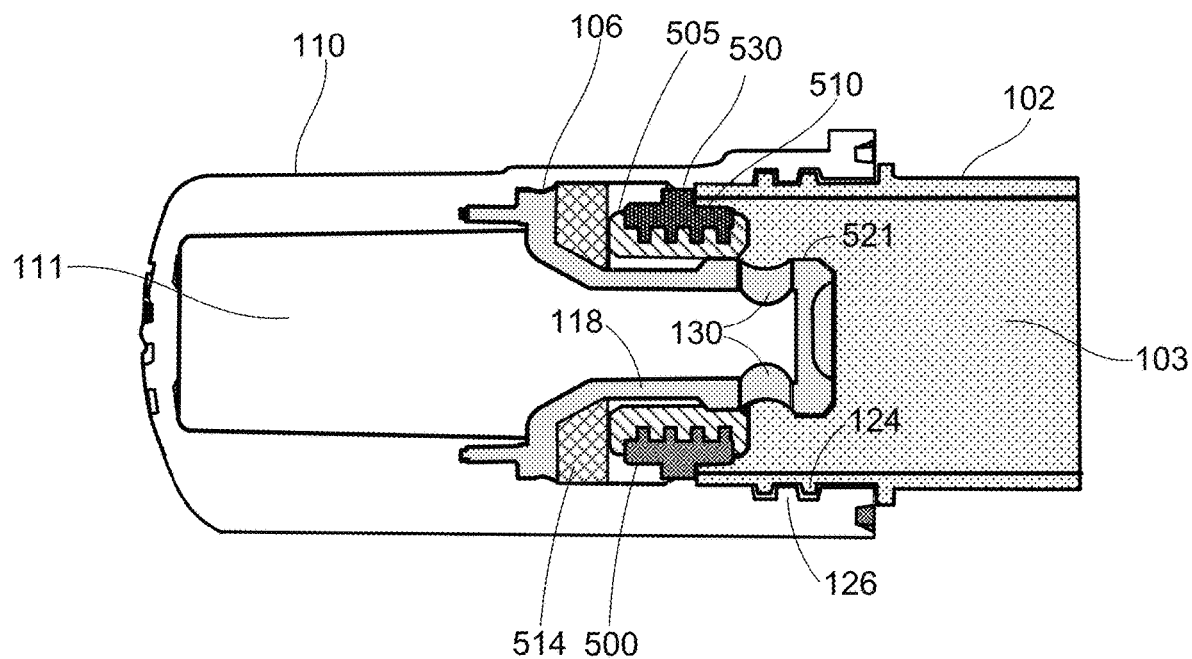

FIGS. 5L and 5M illustrate interactions between the sealing cap 110 and the sample collection vessel 102 when the sample collection vessel 102 engages with the sealing cap 110, in accordance with an embodiment. The outer sleeve 500 includes an exterior ridge 530, which is a protrusion from the exterior face of the outer band 510. The exterior ridge 530 enables the translational movement of the outer sleeve 500 over and away from the fluid vents 130. FIG. 5L illustrates a side view of a cross-section of a sample collection system 100 with an outer sleeve 500 engaged with a sample collection vessel 102. To release preservation reagent stored in the reagent chamber 111 of the sealing cap 110, a user screws the sealing cap 110 onto the sample collection vessel 102 that may carry the user's biological sample. The engaging of the sealing cap 110 to the sample collection vessel 102 and the continuing screwing of the sealing cap 110 onto the sample collection vessel 102 cause an upper rim 213 (also labeled in FIG. 1) of the sample collection vessel to make contact with the opposing edge of the exterior ridge 530 of the outer sleeve 500, as illustrated in FIG. 5L.

As a user continues to screw the sealing cap 110 onto the sample collection vessel 102, the resulting contact between the sample collection vessel 102 and the exterior ridge 530 overcomes the compression force that forms the fluid-tight seal over the fluid vents 130 and raised surface area 521 adjacent to the fluid vents 130, causing the outer sleeve 500 to slide translationally along the exterior sidewall 118 of the inner vessel, exposing the fluid vents 130. The sealing cap 110 may include a first set of screw threads 126 and the sample collection vessel 102 may include a second set of screw threads 124 that are complementary to the first set of screw threads 126. Before the sample collection vessel 102 makes contact with the outer sleeve 500, the user may feel a relatively easy movement of the sealing cap 110. In one example embodiment shown in FIG. 5L, the outer sleeve 108, in the closed position, may translationally overlap with at least a portion of the first set of screw threads 126. After the sealing cap 110 is partially engaged with the sample collection vessel 102 and the sample collection vessel 102 begins to make contact with the outer sleeve 500, the user may feel additional resistance for the further screwing of the sealing cap 110 onto the sample collection vessel. In some embodiments, a signal may be provided to the user that the preservation reagent will be released into the sample collection vessel 102. When the sealing cap 110 is fully engaged with the sample collection vessel 102 (e.g., fully screwed on), the sample collection vessel 102 will have pushed the outer sleeve 500 to the open position, thereby opening the fluid vents 130. When the sealing cap 110 is fully engaged with the sample collection vessel 102, the outer sleeve 500 is displaced away from the first set of screw threads 126, as shown in FIG. 5K in the open position.

FIG. 5M illustrates a side view of a cross-section of a sample collection system 100 with an outer sleeve 500 engaged with a sample collection vessel 102 to expose fluid vents 130 of the inner vessel 106. Once exposed, preservation reagent flows through the fluid vents 130 into the sample collection chamber 103 of the sample collection vessel 102. Additionally, while shifting the outer sleeve 500 along the exterior sidewall 118 to expose the fluid vents 130, the sample collection vessel 102 locks in place by connection members 124 (e.g., complementary threads) on the exterior sidewall of the sample collection vessel 102 with connection members 126 (e.g., complementary threads) on an interior sidewall the sealing cap 110. In one embodiment, in a fully engaged configuration, outer sleeve 500 is pushed in until it meets a cap band 514 so that the outer sleeve 500 is held in place between the cap band 514 and the sample collection vessel 102. The cap band 514 may serve as a hard stop for the outer sleeve 500. When the sample collection vessel 102 is locked in place, the outer sleeve 500 forms a fluid-tight seal against the exterior sidewall 118 of the inner vessel 106. The outer sleeve 500 is also in contact with the top surface of the sample collection vessel 102. In some embodiments, the contact between the outer sleeve 500 and the sample collection vessel 102 can form a fluid-tight seal. In some embodiments, the inner vessel 106, the outer sleeve 500, and the sample collection vessel 102 cooperate to form an enclosed environment for the biological sample. The formed fluid-tight seal prevents preservation reagent from flowing into open spaces in the sealing cap 110 and directs fluid flowing out of the fluid vents 130 into the sample collection chamber 103 of the sample collection vessel 102. In some embodiments, the inner vessel 106 may be retained in an engaged position with the sealing cap 110 by use of a number of joining methods, such as, but not limited to, a snap fit, a press fit, a compression fit, a chemical bond, a UV bond, induction welding, thermal welding, adhesives, fasteners, and/or other applicable means, or a combination thereof, for retaining the engagement of the inner vessel 106 to the sealing cap 110. The cap band 514 may also help to securely retain the inner vessel 106 in the sealing cap 110.

As shown in FIGS. 2 and 3, the selectively movable sleeve valve 104 can be configured in a closed configuration (FIG. 2) and an open configuration (FIG. 3). In the open configuration illustrated in FIG. 3, the inner vessel 106 protrudes through the outer sleeve 108. As discussed above with respect to various FIGS. 5 and 6, this causes a region of the inner vessel 106 having a diameter d2 to be associated with the distal end of the outer sleeve 108 (e.g., the region associated with d3). In some embodiments, the outer sleeve 108 can be made of a material configured to flex under such strain, allowing the larger diameter portion d2 to extend through the distal end of the outer sleeve 108, as shown in FIG. 3. For example, the outer sleeve may be made of polypropylene or a thermoplastic elastomer. The properties of the material should allow for a fluid-tight seal between the inner vessel 106 and the outer sleeve 108 and also allow the selectively movable sleeve valve 104 to move between open and closed positions.

In some embodiments, when the inner vessel 106 protrudes through the outer sleeve 108, causing the outer sleeve 108 to elastically flex (e.g., when the selectively movable sleeve valve 104 is in an open configuration), the tapered nature of the exterior sidewall 118 and the interior sidewall 122 defining the aperture 134 can cause the selectively movable sleeve valve 104 to return to a closed configuration (as shown in FIG. 2) when whatever force that is being applied to cause the open configuration is relieved (e.g., the sealing cap 110 is loosened). Upon relief of the force causing the open configuration, the elastically flexed outer sleeve 108 can provide sufficient force to move the inner vessel 106 back through the aperture 134.

Accordingly, in some embodiments, tightening the association of the sealing cap 110 with the sample collection vessel 102 forces the selectively movable sleeve valve 104 into an open configuration where the outer sleeve 108 is elastically flexed, and loosening the association of the sealing cap 110 with the sample collection vessel 102 allows the outer sleeve 108 to return to a less flexed state, pushing the inner vessel 106 back into the aperture 134, obstructing fluid vents 130, and returning the selectively movable sleeve valve 104 to a closed position.

Figure 7:
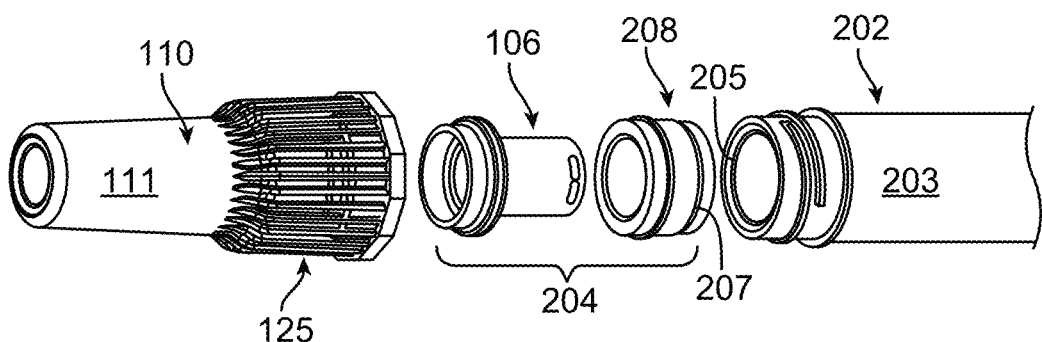
FIG. 7 illustrates an exploded perspective view of a three-dimensional model of a sample collection system that includes a cap configured to receive a selectively movable sleeve valve.

In FIGS. 2 and 3, the inner vessel 106 and the outer sleeve 108 contact one another through frictional fit. In some embodiments, the open and closed configurations may be defined by any suitable spatial relationship between the inner vessel 106 and the outer sleeve 108. For example, the fluid vents 130 of the inner vessel 106 may be in a rotational relationship with a portion of the wall of the outer sleeve 108 covering the fluid vents 130. Put differently, in the closed configuration, the fluid vents 130 may be in a first rotational position relative to the outer sleeve 108 so that the fluid vents 130 are covered by the interior wall of the outer sleeve 108. The outer sleeve 108 may include an opening or have a shape, such as a recess or such as by plastic deformation, that may serve as an opening. From the closed position, the fluid vents 130 may be rotated and be in a second rotational position, relative to the outer sleeve 108, so that the fluid vents 130 lines up with the opening of the outer sleeve 108 to allow the preservation reagent to release. In another embodiment, the open and closed positions may be defined by a longitudinal spatial relationship between the inner vessel 106 and outer sleeve 108. For example, in a transition from a closed position to an open position, the inner vessel 106 may be moved longitudinally relative to the outer sleeve 108, thereby exposing the fluid vents 130 and allowing the preservation reagent to be released. In yet another embodiment, the open and closed positions may be defined by a combination of rotational and longitudinal relationships. As shown in FIG. 7, some embodiments of the present disclosure include a sample collection system 200 having a sample collection vessel 202, a sleeve valve 204 that can be selectively and reversibly opened and closed and which comprises an outer sleeve 208 and an inner vessel 106, and a sealing cap 110 operable to cover and seal the opening of the sample collection vessel 202. The outer sleeve 208 can include a detent 207 that mates with or otherwise selectively associates with a ring structure 205 disposed on an interior sidewall 203 of the sample collection vessel 202. When assembled, the detent-ring association can enable or assist the sleeve valve device 204 in being selectively and, if desired, reiteratively opened and closed.

Various features and configurations shown in different embodiments of the sample collection system in FIG. 5A through 5M can be combined. For example, the inner vessel 106 with features shown in FIG. 5B or FIG. 5E can be used as the inner vessel 106 in FIG. 5J. The features used in the coupling between the sealing cap 110 and the inner vessel 106, such as using a cap band 514 and/or using interference fit, may also be used in any of the embodiments of the sample collection system.

In various embodiments, the inner vessel 106 may take different forms and be coupled with different materials. For example, as shown in FIG. 5A, the inner vessel 106 may be formed of a single material with a flat profile to the right of the retaining ring 114. In another example shown in FIGS. 5B and 5C, the inner vessel 106 with the raised surface area 119 may also be formed as a single integrated article (e.g., injection molded as a single piece) including raised ridges 121 and recesses 560. In yet another example, shown in FIGS. 5E and 5F, the raised surface area 119 is a separate component that may be formed of a different material than the inner layer 516 of the inner vessel 106. The two components being securely coupled to each other make an inner vessel 106. The raised surface area 119 is referred to as a sleeve band 503, which is shaded in the Figures. The sleeve band 503 may be coupled to the inner layer 516 of the inner vessel 106 at the interface of the inner vessel 106 by various methods, including but not limited to, overmolding, frictional fit, adhesives, chemical bonding, thermal welding, mechanical features, or any combination thereof.

Other forms and combinations of inner vessel 106 are also possible. In one embodiment, the inner vessel 106 includes raised surface area 119 that may take the form of ribs, raised features, snap fit features, press fit features, etc. In one embodiment, the inner vessel 106 includes a sleeve band 503 with or without raised surface area 119. In one embodiment shown in FIGS. 5J through 5M, the inner vessel 106 which includes a cap band 514 on the exterior surface of the inner vessel 106 where it engages with the sealing cap 110 to form a fluid-tight seal. In one embodiment, the cap band 514 on the exterior surface of the inner vessel 106 may or may not include a raised surface area 119. In one embodiment, the inner vessel 106 may include both a sleeve band 503 and a cap band 514. In one embodiment, the inner vessel 106 includes a cap band 514 and a sleeve band with a raised surface area 119. In one embodiment, both the cap band 514 and sleeve band 503 both include raised surface areas. Other embodiments may include any combinations of various features described above.

Various components in the sample collection system, such as the inner vessel 106, outer sleeve 108, and sealing cap 110, may take the form of a single integrated material or may include multiple layers that are made of different materials. For example, at an interface of two components (e.g., between inner vessel 106 and sealing cap 110, between inner vessel 106 and outer sleeve 108, etc.), at least one of the components may, or the two components may each, include a layer that is made of a softer and more elastic material to improve sealing at the interface. Sleeve band 503 of the inner vessel 106 shown in FIG. 5E, inner layer 505 of the outer sleeve 500 shown in FIG. 5I, and cap band 514 of the inner vessel 106 shown in FIG. 5J are examples of those sealant layers. The sealant layers may be made of suitable materials such as thermoplastics and its variants (e.g., thermoplastic elastomers, thermoplastic vulacnizates), soft rubber, silicone, etc. In addition to the softer sealant layer, one or more of the various components of the sample collection system may include a stiffer layer to provide mechanical support to the component. The inner layer 516 of the inner vessel 106 shown in FIG. 5J and outer band 510 of the outer sleeve 500 are examples of those structural layers. The structural layers may be made of suitable materials that provide sufficient strength to the sample collection system. Example materials may include suitable polymeric materials such as polypropylene, polycarbonate, fiber glass, etc.

In various embodiments of the sample collection system, various components or their layers may be securely coupled to other components or other layers. For example, the sealing cap 110 and the inner vessel 106 may be securely coupled to each other. Likewise, the inner band 505 and the outer band 510 are securely coupled to each other to form the outer sleeve 500. The secured coupling between two components (including coupling of two layers) may be achieved by one or more methods, including but not limited to, interference fit (press fit, friction fit), compression fit, snap fit, mechanical features, chemical bonding, material interaction (e.g. swelling), solvent bonding, interference fit with snap fit, interference fit with mechanical features, interference fit with chemical bonding, interference fit with solvent bonding, interference fit with material interaction, compression fit with snap fit, compression fit with mechanical features, compression fit with chemical bonding, compression fit with solvent bonding, compression fit with material interaction, interference fit with snap fit with chemical bonding, interference fit with snap fit with solvent bonding, interference fit with snap fit with material interaction, interference fit with mechanical features with chemical bonding, interference fit with mechanical features with solvent bonding, interference fit with mechanical features with material interaction, any combination thereof, or any other suitable methods not explicitly described.

Methods Implementing a Sealing Cap Having a Selectively Movable Sleeve Arm

With continued reference to FIGS. 1-6, an exemplary method for implementing a multi-part sample collection kit, as described above, includes receiving a biological sample through a funnel connected to the sample collection vessel 102. The received biological sample can enter directly into the sample collection vessel 102 or by gravitational flow along an interior funnel sidewall. The method can additionally include removing the funnel from the sample collection vessel 102 after facilitating receipt of the biological sample, and associating a sealing cap 110 with the sample collection vessel 102. The method can additionally include securing the sealing cap 110 (e.g., by rotating the sealing cap 110 along complementary threads between the cap 110 and the collection vessel 102) to close the cap 110 over the top of the sample collection vessel 102. The sealing cap 110 can contain preservation reagent(s) that are released as the sealing cap 110 is rotated and closed over the sample collection vessel 102. In some embodiments, a selectively movable sleeve valve 104 associated with the sealing cap 110 undergoes a conformational change when the sealing cap 110 is rotated and closed over the collection vessel 102.

As shown in FIGS. 2 and 3, the sealing cap 110 secures to and seals the collection vessel 102 and can do so by any means described herein or as known in the art. In this closed and sealed state, the selectively movable sleeve valve 104 is in an open configuration, and the reagent(s) mix with the collected sample. The collection vessel 102 can be shaken to allow all or at least most of the preservation reagent to cover the collected sample. Additionally, the biological sample therewithin is beneficially protected from the outside atmosphere by being air- and water-tight. This reduces the chances of the sample contamination and helps maintain the integrity of the probative component during transportation to the laboratory.

In some embodiments, the sealing cap is under pressure and moving the selectively movable sleeve valve into an open position causes the preservation reagent(s) stored within the sealing cap to be forcefully expelled into the sample collection chamber. This can beneficially encourage stored reagent(s) to mix with the collected sample and may additionally act to preserve the reagent(s) and/or the probative component thereof.

Methods can additionally include removing the preserved sample from the sample collection system 100. This can involve, for example, the steps of unscrewing or otherwise removing the sealing cap 110 from the sample collection vessel 102. In doing so, the outer sleeve 108 can be retained by the sample collection vessel 102 while the sealing 110 cap and associated inner vessel 106 are drawn away from the sample collection vessel 102. This can cause the sleeve valve 104 to reseal (e.g., return to a closed configuration). Further disassociation of the sealing cap 110 from the sample collection vessel 102 can cause the sleeve valve 104 to be removed in a resealed state, exposing the opening of the sample collection vessel 102 and allowing access to the preserved biological sample.

Figure 8:
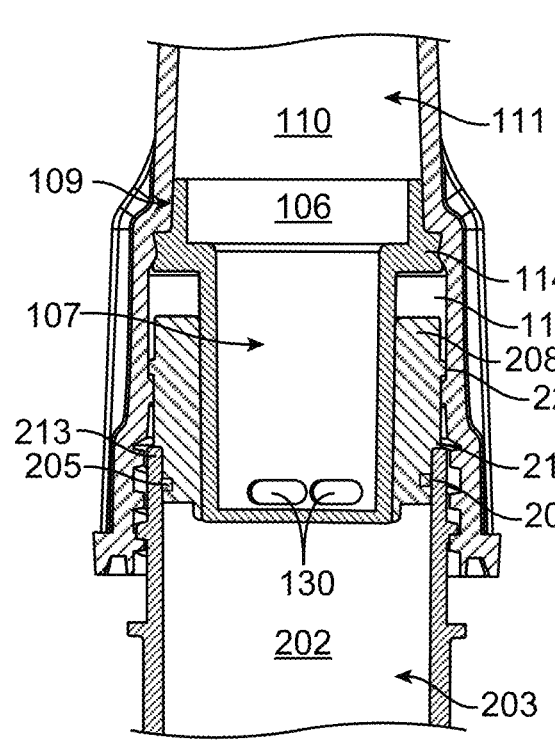
FIG. 8 illustrates a cross-sectional view of a sample collection system with a selectively movable sleeve valve depicted in a closed position.
Figure 9:
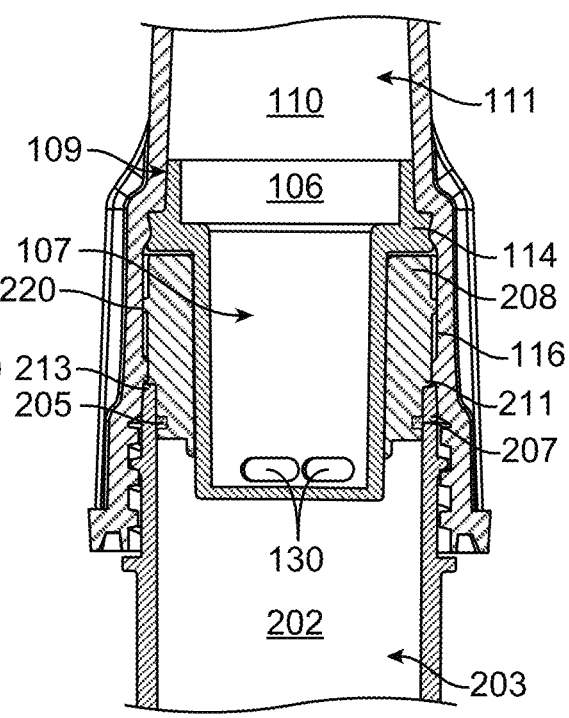
FIG. 9 illustrates a cross-sectional view of a sample collection system with a selectively movable sleeve valve depicted in an open position.

Referring now to FIGS. 8 and 9, an exemplary use of a sample collection system 200 can include a sealable and/or resealable sleeve valve 204. For example, during assembly of the sealing cap 110 with the associated sleeve valve 204, the reagent chamber 111 of the sealing cap 110 can be filled with a measure of sample preservation reagent(s). The inner vessel 106 of the sleeve valve 204 can then be press-fit into and retained by the sealing cap 110. As shown in FIGS. 8 and 9, the inner vessel 106 defines a reagent retention chamber 107 that is in fluid communication with the reagent chamber 111 of the sealing cap 110 and further defines a plurality of fluid vents 130 through which reagent within the reagent chamber 111 can be delivered to a collected sample. An upper collar 109 of the inner vessel 106 extends into—and provides an interference fit with—the reagent chamber 111 of the sealing cap 110, and a retaining ring 114 defined by the inner vessel receives a complementary protrusion 112 from the sealing cap 110 sidewall, further anchoring the inner vessel 106 within the sealing cap 110 to prevent separation. Together (or individually) these components of the inner vessel 106 can act to provide a fluid-tight seal between the inner vessel 106 and the solution cap 110.

In the exemplified embodiment, the combination of inner vessel 106 and outer sleeve 208 comprises the sleeve valve 204, which can be selectively and reversibly moved between a sealed configuration 200A and an unsealed configuration 200B. When the outer sleeve 208 is associated with the inner vessel 106 in the sealed configuration 200A, it can prevent the premature or unintentional expulsion of reagent from the sealing cap 110.

Assembly of the sleeve valve 204 can occur before, during, or after the inner vessel 106 is attached to the sealing cap 110. It can involve advancing the outer sleeve 208 over the inner vessel 106 and within the sealing cap 110 until an exterior-facing guide member 220 on the outer sleeve is received (e.g., snap-fittedly received) into a guide channel 116 of the sealing cap 110. Once the outer sleeve 208 has been advanced over the inner vessel 106 and the guide member 220 received within the guide channel 116 of the sealing cap 110, the outer sleeve 106 is in an initially sealed configuration 200A, thereby covering the fluid vents 130 of the inner vessel 106 and sealing and retaining the sample preservation reagent(s) inside the sealing cap 110 and inner vessel 106 (e.g., as illustrated in FIG. 2 but before the sealing cap has been placed onto the sample collection vessel).

The guide channel 116 of the sealing cap 110 can be sized to allow limited translational movement of the guide member 220 within the guide channel 116. This, in turn, restricts the movement of the inner vessel 106 relative to the outer sleeve 208 when the sealing cap 110 is secured and unsecured from the sample collection vessel 202 (e.g., as illustrated in FIGS. 8 and 9 when the sealing cap 110 is secured to the sample collection vessel 202, causing the selective unsealing of the sleeve valve 204). An inner facing edge or protrusion of the sealing cap 110 can define a lower end of the guide channel 116 and can act to retain the guide member 220 within the guide channel 116, preventing separation of the outer sleeve 208 from the sealing cap 110 when the sealing cap 110 is decoupled from the sample collection vessel 202.

In an exemplary use, the sample collection vessel 202 is used to receive a biological sample through the opening of and into the sample collection vessel 202 (e.g., receiving saliva through an optional funnel temporarily attached to the sample collection vessel 202). After the biological sample is received within the sample collection vessel 202, the user can place the sealing cap 110 over the sample collection vessel 202, with the sleeve valve 204 facing the opening of the sample collection vessel 202 and advance the sleeve valve 204 into the opening of the sample collection vessel 202. When the sleeve valve 204 is advanced through the opening of the sample collection vessel 202, a detent 207 formed within the lower collar of the outer sleeve 208 can mechanically engage a protruding retention ring 205 on the interior sidewall 203 of the sample collection vessel 202. The ring-detent engagement can prevent the sleeve 204 from being pushed farther into the sample collection vessel 202, but in some variations, the body 211 of the outer sleeve 208 above the lower collar abuts an upper rim 213 of the sample collection vessel 202, thereby preventing the sleeve 204 from being pushed any farther into the sample collection vessel 202.

Further advancement of the sealing cap 110 toward the sample collection vessel 202, including engagement of complementary interlocking threads located on the sealing cap 110 and the sample collection vessel 202, can force the inner vessel 106 through the outer sleeve 208 and affect a conformational change in the sleeve valve 204 from the sealed position 200A shown in FIG. 8 to the unsealed position 200B shown in FIG. 9. Moving the sleeve valve 204 from the sealed position 200A to the unsealed position 200B un-occludes the fluid vents 130 and allows the reagent(s) to flow into the sample collection vessel 202.

The foregoing unsealing of the sleeve valve can be temporary and reversible. For example, when the sealing cap 110 is removed from the sample collection vessel 202 to recover the biological sample, the sleeve valve 204 can be restored to the sealed configuration 200A, reestablishing the seal between the outer sleeve 208 and inner vessel 106. As the sealing cap 110 is unscrewed from the sample collection vessel 202, in some embodiments, the outer sleeve 208 can be temporarily retained in a fixed position within the sample collection chamber while the inner vessel 106 is withdrawn, causing the outer sleeve 208 to re-occlude the fluid vents 130 (e.g., moving the sleeve valve 204 from the unsealed configuration 200B of FIG. 9 to the resealed configuration 200A of FIG. 8). The outer sleeve 209 can be temporarily retained in the fixed position due to the retention ring 205 within the sample collection vessel 202 mechanically engaging with the detent 207 on the lower collar of the outer sleeve 208. The frictional forces between the outer sleeve 208 and inner vessel 106 can be less than the force required to disengage the ring-detent interaction, allowing such relative movement.

When the inner vessel 106 has been withdrawn relative to the outer sleeve 208 so as to reseal the fluid vents 130, the guide member 220 can reach the end of the guide channel 116 where further movement is impeded by the inner facing edge or protrusion of the sealing cap 110. The sample collection system 200 is designed in some embodiments so that the sealing cap 110 and sleeve valve 204 can—at this point—be removed from the sample collection vessel 202 without the catastrophic failure of any components. That is, the sample collection system 200 can be designed so that the detent 207 on the outer sleeve 208 can be disengaged from the protruding ring 205 of the sample collection vessel 202 while maintaining the integrity of the sealing cap-sleeve valve association. This can be enabled, for example, by engineering the components such that the mechanical force required to disengage the ring 205 and detent 207 is less than the force required to remove the guide member 220 from the guide channel 116. Further withdrawal of the sealing cap 110 from the sample collection vessel can, therefore, overcome the ring-detent interaction, permitting the sealing cap 110, inner vessel 106, and outer sleeve 208 to be removed as a single unit from the sample collection vessel 202—with the valve 204 in the resealed configuration 200A.

It should be appreciated that although the foregoing embodiment depicted the ring 205 being associated with the sample collection vessel 202 and the detent 207 being associated with the outer sleeve 208, in some embodiments, the attachment mechanism between the two components may be switched or replaced by other complementary components that perform the same or similar function. For example, the sample collection vessel may include a detent within an interior sidewall that associates with a ring structure disposed on the outer sleeve.

Figure 10:
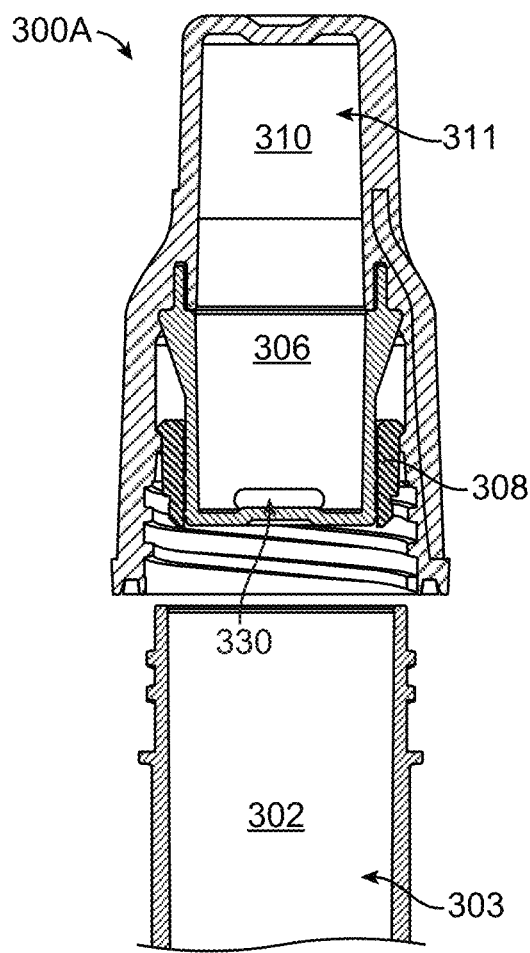
FIG. 10 illustrates a cross-sectional, unassembled view of a sample collection system with a selectively movable sleeve valve depicted in a closed position.
Figure 11:
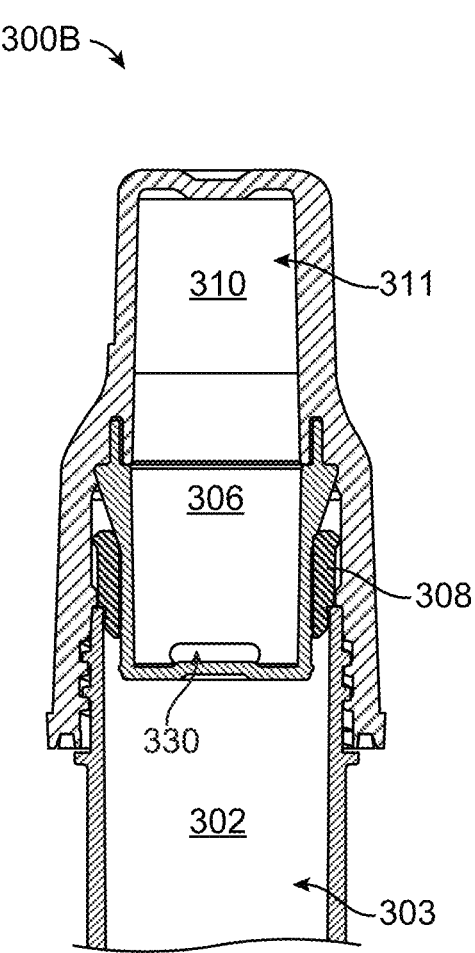
FIG. 11 illustrates a cross-sectional, assembled view of a sample collection system with a selectively movable sleeve valve depicted in an open position.

FIGS. 10 and 11 illustrate a cross-sectional, unassembled view 300A and a cross-sectional, assembled view 300B, respectively, of an additional embodiment of a sample collection system 300 with a selectively movable sleeve valve 304 depicted in an unsealed configuration and in a sealed/resealed configuration, respectively.

Similar to the embodiments of FIGS. 1-9, the system 300 includes a collection vessel 302 and optionally, a funnel (not shown), which can be associated with a top portion of the collection vessel 302 and in fluid communication with a sample collection chamber 303 of the collection vessel 302. The biological sample collection system 300 can also include the selectively movable sleeve valve 304 comprised of an inner vessel 306 and an outer sleeve 308 associated with a sealing cap 310 that has a reagent chamber 311 disposed within or integrated with the sealing cap 310. The sealing cap 310—together with the selectively movable sleeve valve 304—can be sized and shaped to associate with a top portion of the sample collection vessel 302, fitting over and sealing an opening of the sample collection chamber 303. For the sake of clarity, the description for corresponding components of the systems 100 and 200 applies to the system 300 and is incorporated herein.

Figure 12:
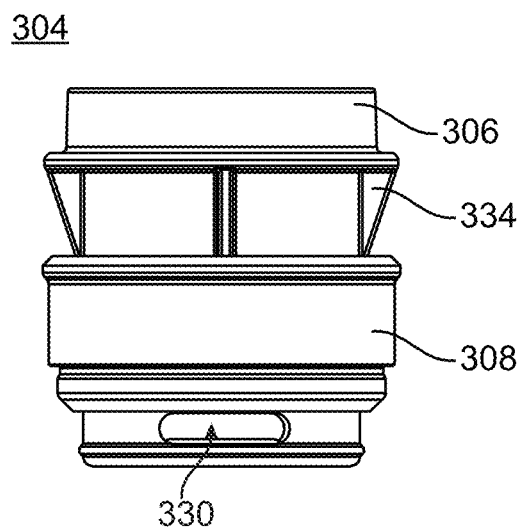
FIG. 12 illustrates the selectively movable sleeve valve of FIGS. 10 and 11 in an open position.

In the exemplified embodiment, the combination of inner vessel 306 and outer sleeve 308 comprises the sleeve valve 304, as shown in FIG. 12. The sleeve valve 304 can be selectively and reversibly moved between the sealed configuration 300A and the unsealed configuration 300B. When the outer sleeve 308 is associated with the inner vessel 306 in the sealed configuration 300A, it can prevent the premature or unintentional expulsion of reagent from the sealing cap 110 through the fluid vent 330. In the embodiments of FIGS. 10-12, the outer sleeve 308 encircles a bottom portion of the inner vessel 306 where the fluid vent 330 is positioned. The inner vessel 306 comprises a plurality of ribs 334 about an upper portion of the inner vessel 306. The plurality of ribs 334 may be spaced evenly or at varying intervals about the outer surface of the inner vessel 306.

After a biological sample is received within the sample collection vessel 302, the user can place the sealing cap 310 over the sample collection vessel 302, with the sleeve valve 304 facing the opening of the sample collection vessel 302 and advance the sleeve valve 304 into the opening of the sample collection vessel 302. When the sleeve valve 304 is advanced through the opening of the sample collection vessel 302 toward the sample collection vessel 302, including engagement of complementary interlocking threads located on the sealing cap 310 and the sample collection vessel 302, it can force the inner vessel 306 through the outer sleeve 308 and affect a conformational change in the sleeve valve 304 from the sealed position 300A shown in FIG. 10 to the unsealed position 300B shown in FIG. 11. The outer sleeve 308 is moved towards the plurality of ribs 334. Moving the sleeve valve 304 from the sealed position 300A to the unsealed position 300B un-occludes the fluid vents 330 and allows the reagent(s) to flow into the sample collection vessel 302.

Figure 13A:
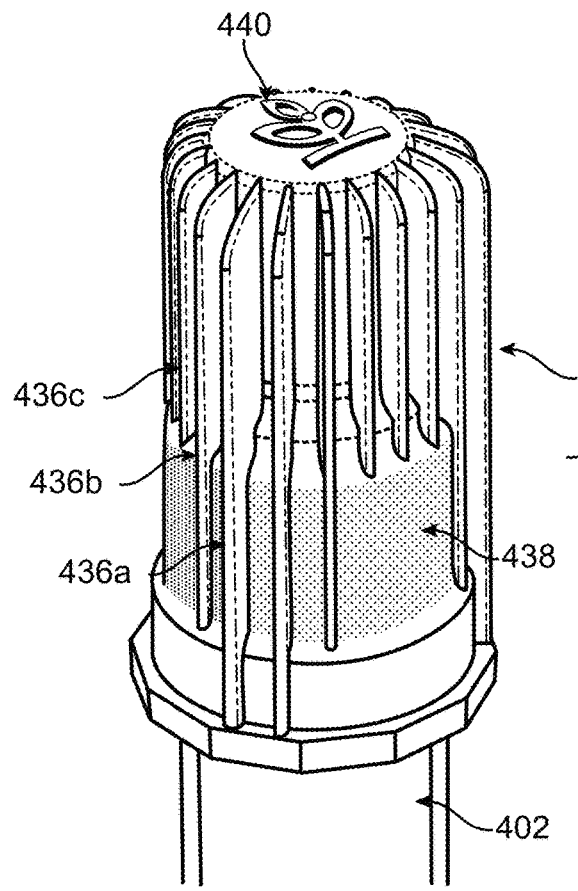
FIGS. 13A-13G illustrate perspective, elevated, and cross-sectional views of various embodiments of a sealing cap.
Figure 13B:
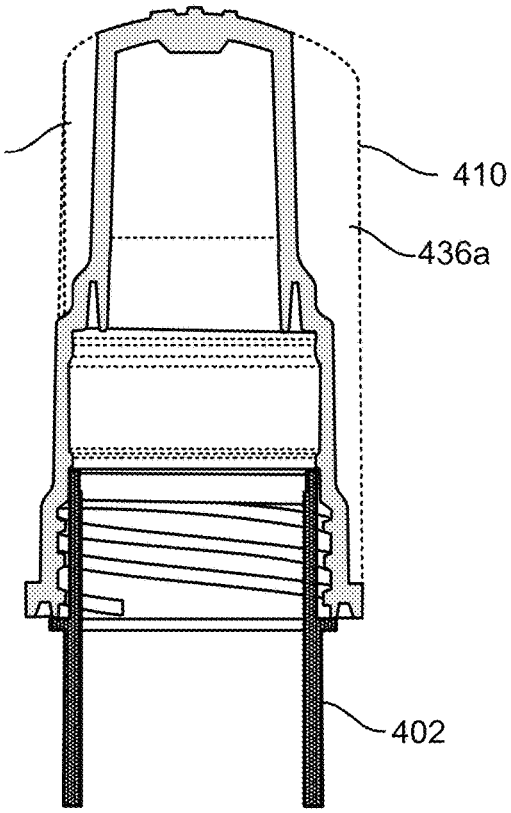
Figure 13C:
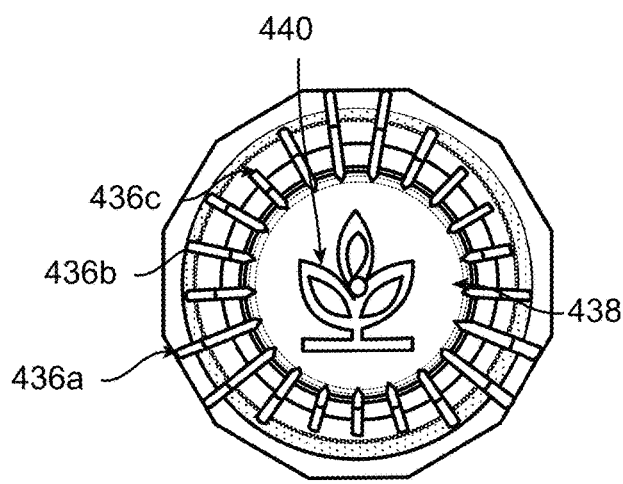

FIGS. 13A-13C illustrate a perspective view, a cross-sectional view, and a top view of a sealing cap 410. The design of a sealing cap may have various functional features, for example that enable a user to conveniently and reliably associate the sealing cap and the sample collection vessel, and various aesthetic features, such as a brand or logo. As described with regard to the embodiments of FIGS. 1-9, applying a rotational force threadedly associates the sealing cap 410 and the sample collection vessel 402, and applying a directionally opposite rotation force disassociates the sealing cap and the sample collection vessel. In the embodiments of FIGS. 13A-13C, the sealing cap 410 comprises a plurality of gripping features 436 about an outer surface 438 and a logo 440. The plurality of gripping features 436 enable a user to grip the sealing cap to apply a rotational force to associate and disassociate the sealing cap with the sample collection vessel. While the geometry of the outer surface 438 may vary, the sealing cap generally has a cylindrical core. The plurality of gripping features 436 may vary in shape, length, arrangement, and orientation.

Figure 13D:
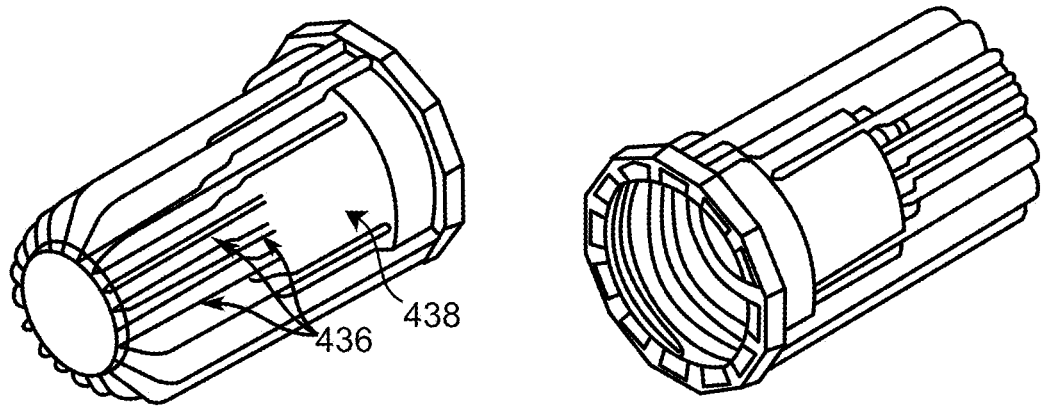
Figure 13E:
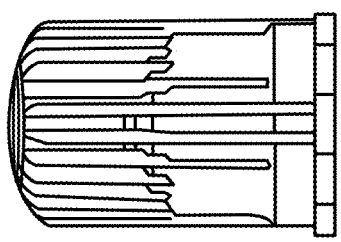
Figure 13F:
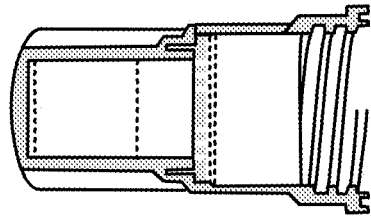
Figure 13G:
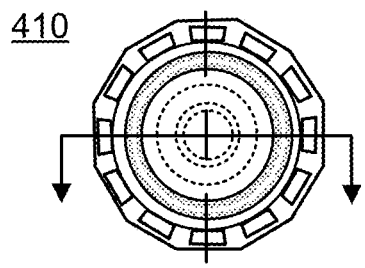

FIG. 13D illustrates a front view and a rear view of a sealing cap with a design of the outer surface 438 of the sealing cap that is wide enough for a user to effectively grip the sealing cap 410 when coupling the cap to an inner vessel 306. Alternatively, the sealing cap 410 may be designed to include a plurality of elongated and protruding gripping features 436a from the outer surface to improve a user's ability to apply a rotational force to the sealing cap. In one embodiment, the gripping feature 436a may extend substantially from the top to the bottom of the sealing cap 410. In one embodiment, the elongated gripping features 436a are distributed radially at different rotational positions of the sealing cap 410. For example, a sealing cap 410 may have a few pairs of the elongated gripping features 436a distributed radially. As a result, when associate the sealing cap 410 with the collection vessel 402 via the threaded features, the user is able to apply more torque to the sealing cap 410 resulting in a more effective liquid-tight seal. Additionally, the seal cap may be designed to prevent a user from associating the cap with the collection vessel by applying a normal longitudinal force to the exterior face of the seal cap 410 and instead prompt the user to apply a rotational force to couple the threaded interior of the seal cap 410 with the threaded exterior of the collection vessel 402. The rotational force may force a rotation between the inner vessel 106 and the outer sleeve 108, thereby opening the fluid vent 130 and releasing the preservation reagent. FIG. 13E illustrates a side view of a sealing cap 410 designed to be wide enough for a user to effectively grip the sealing cap 410, according to one embodiment. In some embodiments, for example the embodiment illustrated in FIG. 13F, the interior of the sealing cap 410 is lined with threading mechanisms that correspond to threading mechanism on the exterior of outer vessel configured to couple to the sealing cap 410. FIG. 13G illustrates a top view of a sealing cap designed to be wide enough for a user to effectively grip the sealing cap, according to one embodiment.

As illustrated in FIGS. 13A-13G, the outer surface 438 has a cylindrical core with three portions, each having different diameters. The gripping features 436 are elongated ribs that are equally and radially spaced about the outer surface 438. A length of each gripping feature 436 may vary; FIG. 13A illustrates a plurality of long ribs 436a, medium ribs 436b, and short ribs 436c, corresponding to the differing diameters of the outer surface 438. The gripping features 436 are arranged in a pattern, but in other embodiments they may be arranged differently (e.g., at varying intervals). As shown in the top view in FIG. 13C, a height of each gripping feature 436 (in a perpendicular direction relative to the outer surface 438) may also vary. FIG. 13C illustrates the plurality of gripping features 436 forming approximately a triangular shape about the outer surface 438, where a height of each gripping feature 436 corresponds to a length of each gripping feature 436. In other words, the gripping features 436 with the longest length are the tallest in height, 440 the gripping features 436 with the shortest length are the shortest in height. FIG. 13C illustrates the logo 440 positioned on the outer surface 438 in the center of the radially spaced gripping features 436.

Figure 14N:
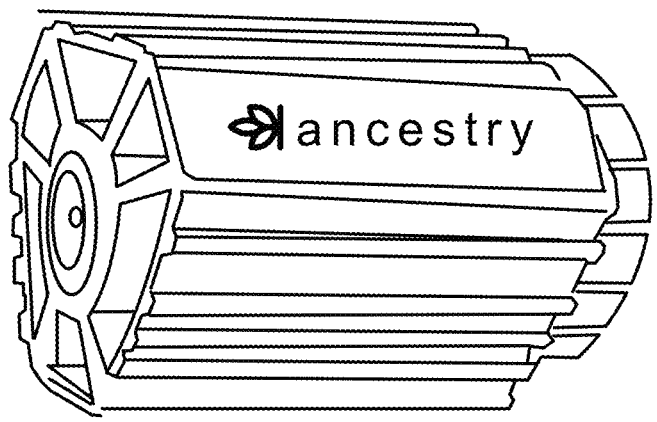
FIGS. 14A-14N illustrate various embodiments of a sealing cap.

FIGS. 14A-14N illustrate perspective views of various embodiments of a sealing cap. As previously described, the design of a sealing cap may have various functional features, for example that enable a user to conveniently and reliably associate the sealing cap and the sample collection vessel, and various aesthetic features, such as a brand or logo. While the geometry of the outer surface of the sealing cap may vary, the sealing cap generally has a cylindrical core. The gripping features on the outer surface may vary in shape, length, arrangement, and orientation, or similar.

FIG. 14A illustrates an embodiment of a sealing cap 1400 that includes an outer surface and a plurality of gripping features. In the embodiment of FIG. 14A, the outer surface is substantially cone-shaped, and the plurality of gripping features are elongated ribs that are radially and equally spaced about the outer surface. The elongated ribs extend from a top edge of the sealing cap 1400 to a bottom edge of the sealing cap 1400. Two gripping features that are positioned opposite each other protrude a greater distance from the outer surface than the remaining gripping features, creating two "wings" for gripping the sealing cap 1400.

FIG. 14B illustrates an embodiment of a sealing cap 1402 that includes an outer surface and a plurality of gripping features. In the embodiment of FIG. 14B, the outer surface is substantially cone-shaped, and the plurality of gripping features are angled loops that protrude from a bottom portion of the sealing cap 1402. The plurality of gripping features are radially and equally spaced about the outer surface.

FIG. 14C illustrates an embodiment of a sealing cap 1404 that includes an outer surface and a plurality of gripping features. In the embodiment of FIG. 14C, the outer surface is substantially cylindrical with a rounded top edge, and the plurality of gripping features are elongated ribs that are radially and equally spaced about the outer surface. The elongated ribs extend from the top edge of the sealing cap 1404 to about the middle of the sealing cap 1404, covering an upper portion of the sealing cap 1404. On a bottom portion of the sealing cap 1404, the outer surface is smooth and includes a logo.

FIG. 14D illustrates an embodiment of a sealing cap 1406 that includes an outer surface and a plurality of gripping features. In the embodiment of FIG. 14D, the outer surface is about cone-shaped with a rounded top edge, and the plurality of gripping features are elongated ribs that are radially and equally spaced about the outer surface. The elongated ribs extend from the top edge of the sealing cap 1406 to a bottom edge of the sealing cap 1406. The elongated ribs protrude from the outer surface such that the elongated ribs create a substantially cylindrical boundary. On a top portion of the sealing cap 1404, the outer surface includes a logo.

FIG. 14E illustrates an embodiment of a sealing cap 1408 that includes an outer surface and a plurality of gripping features. In the embodiment of FIG. 14E, the outer surface is substantially cylindrical, and the plurality of gripping features are loops that are arranged similar to a flower petal shape. In between the corner loops are elongated ribs. The loops and the elongated ribs extend from the top edge of the sealing cap 1408 to the bottom edge of the sealing cap 1408. On one or more of the loops is a logo.

FIG. 14F illustrates an embodiment of a sealing cap 1410 that includes an outer surface and a plurality of gripping features. In the embodiment of FIG. 14F, the outer surface is substantially cylindrical, and the plurality of gripping features are loops that are arranged similar to a flower petal shape. In between the corner loops are flat surfaces that bridge between the corner loops. The loops and the flat surfaces extend from the top edge of the sealing cap 1410 to the bottom edge of the sealing cap 1410. On one or more of the flat surfaces is a logo.

FIG. 14G illustrates an embodiment of a sealing cap 1412 that includes an outer surface and a plurality of gripping features. In the embodiment of FIG. 14G, the outer surface is substantially rectangular, and the plurality of gripping features are flat surfaces. The flat surfaces extend from near the top edge of the sealing cap 1412 to near the bottom edge of the sealing cap 1412. On top and on bottom of the flat surfaces, a plurality of short ribs extend from the top edge or the bottom edge to the flat surfaces. The short ribs are radially and equally spaced about the outer surface. On one or more of the flat surfaces is a logo.

FIG. 14H illustrates an embodiment of a sealing cap 1414 that includes an outer surface and a plurality of gripping features. In the embodiment of FIG. 14H, the outer surface is substantially rectangular, and the plurality of gripping features are elongated ribs that extend from a top edge of the sealing cap 1414 to a bottom edge of the sealing cap 1414. The elongated ribs are radially and equally spaced about the outer surface.

FIG. 14I illustrates an embodiment of a sealing cap 1416 that includes an outer surface and a plurality of gripping features. In the embodiment of FIG. 14I, the outer surface is substantially rectangular, and the plurality of gripping features are elongated ribs that extend from a top edge of the sealing cap 1416 to a bottom edge of the sealing cap 1416. The elongated ribs are radially and equally spaced about the outer surface. A flat surface extends perpendicularly across the elongated ribs about the outer surface, and on the flat surface is a logo. In the embodiment of FIG. 14I, the flat surface is positioned near a bottom edge of the sealing cap 1416.

FIG. 14J illustrates an embodiment of a sealing cap 1418 that includes an outer surface and a plurality of gripping features. In the embodiment of FIG. 14J, the outer surface is substantially cylindrical, and the plurality of gripping features are loops that protrude from the outer surface. The loops form concave surfaces with adjacent loops, creating a boundary resembling a square with concave surfaces, and the loops extend from near a top edge of the sealing cap 1418 to near a bottom edge of the sealing cap 1418. Near the bottom edge, curved surfaces connect the loops to the bottom edge of the sealing cap 1418. At the top edge, the outer surface is exposed within the loops.

FIG. 14K illustrates an embodiment of a sealing cap 1420 that includes an outer surface and a plurality of gripping features. In the embodiment of FIG. 14K, the outer surface is substantially cylindrical, and the plurality of gripping features are loops that protrude from the outer surface. The loops form concave surfaces with adjacent loops, creating a boundary resembling a triangle with rounded corners and concave surfaces between the corners, and the loops extend from near a top edge of the sealing cap 1418 to a bottom edge of the sealing cap 1418. At the top edge, the outer surface is exposed within the loops. One of the concave surfaces includes a logo.

Figure 14M:
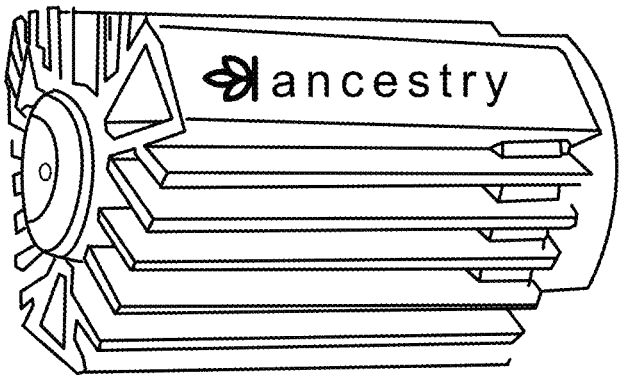
Figure 14L:
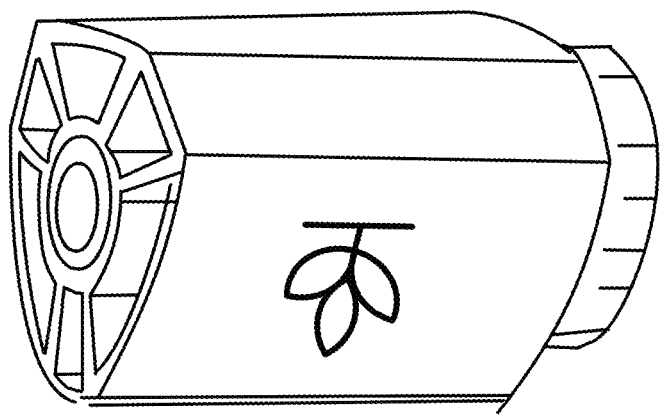

FIG. 14L illustrates an embodiment of a sealing cap 1422 that includes an outer surface and a plurality of gripping features. In the embodiment of FIG. 14L, the outer surface is substantially cylindrical, and the plurality of gripping features are loops that protrude from the outer surface. The loops are flat surfaces, where the loops alternate in size between large and small, creating a boundary resembling a triangle flat corners, and the loops extend from a top edge of the sealing cap 1422 to a bottom edge of the sealing cap 1422. At the top edge, the outer surface is exposed within the loops. One or more of the flat surfaces includes a logo.

FIG. 14M illustrates an embodiment of a sealing cap 1424 that includes an outer surface and a plurality of gripping features. In the embodiment of FIG. 14M, the outer surface is substantially cylindrical, and the plurality of gripping features are elongated ribs that protrude from the outer surface. The elongated ribs create a boundary resembling a triangle flat corners, where the flat corners are formed by loops protruding from the outer surface. The gripping features extend from a top edge of the sealing cap 1424 to a bottom edge of the sealing cap 1424. At the top edge, the outer surface is exposed within the loops. One or more of the loops includes a logo.

FIG. 14N illustrates an embodiment of a sealing cap 1426 that includes an outer surface and a plurality of gripping features. In the embodiment of FIG. 14N, the outer surface is substantially cylindrical, and the plurality of gripping features are loops that protrude from the outer surface. The loops are flat surfaces, where the loops alternate in size between large and small, creating a boundary resembling a triangle flat corners, and the loops extend from a top edge of the sealing cap 1426 to a bottom edge of the sealing cap 1426. On the larger flat surfaces, a plurality of elongated ribs extend along the flat surface. At the top edge, the outer surface is exposed within the loops. One or more of the corner loops includes a logo.

Unless defined otherwise, all technical and scientific terms used herein have the same meaning as commonly understood by one of ordinary skill in the art to which the present disclosure pertains.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A sample collection system, comprising:
  a sample collection vessel for receiving a sample;
  a sealing cap configured to be removably engaged with the sample collection vessel;
  an inner vessel securely engaged with the sealing cap, the inner vessel for storing a reagent, the inner vessel comprising a body characterized as having a first region and a second region, the first and second regions being longitudinal regions of the body and are longitudinally displaced from each other, the inner vessel further comprising a fluid vent located at the first region, the first region having a raised surface area and the second region being recessed compared to the first region; and
  an outer sleeve frictionally engaged with the inner vessel, the outer sleeve slidable longitudinally from the first region to the second region, the outer sleeve at the first region covering the fluid vent and at the second region opening the fluid vent, wherein the raised surface area enhances a friction force between the outer sleeve and inner vessel at the first region compared to the second region.

2. The sample collection system of claim 1, wherein the outer sleeve is configured to be pushed by an edge of the sample collection vessel to slide longitudinally from the first region to the second region.

3. The sample collection system of claim 1, wherein the outer sleeve comprises an inner layer and an outer layer, and the inner layer is made of a first material and an outer layer is made of a second material, different from the first material.

4. The sample collection system of claim 3, wherein the inner layer of the outer sleeve is configured to interact with the inner vessel to create the friction force.

5. The sample collection system of claim 3, wherein the outer sleeve comprises a ridge protruding from an outer surface of the outer sleeve, the ridge is configured to be in contact with a top surface of the sample collection vessel when the sample collection vessel engages with the sealing cap.

6. The sample collection system of claim 1, wherein the inner vessel comprises an edge that is configured to be engaged with a recess at the sealing cap.

7. The sample collection system of claim 1, wherein the sealing cap comprises a first set of screw threads and the sample collection vessel comprises a second set of screw threads that is complementary to the first set of screw threads.

8. The sample collection system of claim 1, wherein the inner vessel comprises a cap band and an inner layer, the cap band positioned between the sealing cap and the inner layer of the inner vessel.

9. The sample collection system of claim 8, wherein the cap band is made of a softer and more elastic material than the inner layer.

10. The sample collection system of claim 8, wherein the cap band is configured to serve as a hard stop of the outer sleeve.

11. A cap for removably engaging with a sample collection vessel for receiving a sample, the cap comprising:
  an outer cap;
  an inner vessel securely engaged with the outer cap, the inner vessel for storing a reagent, the inner vessel comprising a body characterized as having a first region and a second region, the first and second regions being longitudinal regions of the body and are longitudinally displaced from each other, the inner vessel further comprising a fluid vent located at the first region, the first region having a raised surface area and the second region being recessed compared to the first region; and an outer sleeve frictionally engaged with the inner vessel, the outer sleeve slidable longitudinally from the first region to the second region, the outer sleeve at the first region covering the fluid vent and at the second region opening the fluid vent, wherein the raised surface area enhances a friction force between the outer sleeve and inner vessel at the first region compared to the second region.

12. The cap of claim 11, wherein the outer sleeve is configured to be pushed by an edge of the sample collection vessel to slide longitudinally from the first region to the second region.

13. The cap of claim 11, wherein the outer sleeve comprises an inner layer and an outer layer, and the inner layer is made of a first material and an outer layer is made of a second material, different from the first material.

14. The cap of claim 13, wherein the inner layer of the outer sleeve is configured to interact with the inner vessel to create the friction force.

15. The cap of claim 13, wherein the outer sleeve comprises a ridge protruding from an outer surface of the outer sleeve, the ridge is configured to be in contact with a top surface of the sample collection vessel when the sample collection vessel engages with the outer cap.

16. The cap of claim 11, wherein the inner vessel comprises an edge that is configured to be engaged with a recess at the outer cap.

17. The cap of claim 11, wherein the outer cap comprises a first set of screw threads and the sample collection vessel comprises a second set of screw threads that is complementary to the first set of screw threads.

18. The cap of claim 11, wherein the inner vessel comprises a cap band and an inner layer, the cap band positioned between the outer cap and the inner layer of the inner vessel.

19. The cap of claim 18, wherein the cap band is made of a softer and more elastic material than the inner layer.

20. The cap of claim 18, wherein the cap band is configured to serve as a hard stop of the outer sleeve.

* * * * *